United States Patent [19]

Obikawa et al.

[11] Patent Number: 5,238,599
[45] Date of Patent: Aug. 24, 1993

[54] 1,3-DIOXANE DERIVATIVES, METHODS OF PREPARATION AND LIQUID CRYSTAL COMPOSITIONS INCLUDING SAME

[75] Inventors: Tsuyoshi Obikawa; Shuji Ikukawa; Jitsuko Nakayama, all of Suwa, Japan

[73] Assignee: Seiko Epson Corporation, Tokyo, Japan

[21] Appl. No.: 529,100

[22] Filed: May 25, 1990

[30] Foreign Application Priority Data

| May 31, 1989 | [JP] | Japan | 1-138738 |
| Jun. 6, 1989 | [JP] | Japan | 1-143844 |
| Jun. 20, 1989 | [JP] | Japan | 1-157127 |
| Jun. 20, 1989 | [JP] | Japan | 1-157128 |
| Sep. 8, 1989 | [JP] | Japan | 1-233324 |
| Oct. 12, 1989 | [JP] | Japan | 1-265661 |
| Nov. 20, 1989 | [JP] | Japan | 1-301450 |

[51] Int. Cl.$^5$ ............ C09K 19/34; C09K 19/52; C07D 319/06; C07D 407/00
[52] U.S. Cl. ............... 252/299.61; 549/369; 252/299.01
[58] Field of Search ............ 549/369; 252/229.61, 252/229.01

[56] References Cited

U.S. PATENT DOCUMENTS

| 4,344,856 | 8/1982 | Demus et al. | 252/299.61 |
| 4,486,332 | 12/1984 | Demus et al. | 252/299.61 |
| 4,512,636 | 4/1985 | Andrews et al. | 359/103 X |
| 4,551,264 | 11/1985 | Eidenschink et al. | 252/299.62 |
| 4,659,502 | 4/1987 | Fearon et al. | 252/299.61 |
| 4,704,227 | 11/1987 | Krause et al. | 252/299.61 |
| 4,818,428 | 4/1989 | Scheuble et al. | 252/299.1 |

FOREIGN PATENT DOCUMENTS

| 3227916 | 3/1983 | Fed. Rep. of Germany . |
| 3447359 | 3/1986 | Fed. Rep. of Germany . |
| 0260709 | 10/1988 | German Democratic Rep. . |
| 0270922 | 8/1989 | German Democratic Rep. . |
| 2067586 | 7/1981 | United Kingdom . |
| 2092169 | 8/1982 | United Kingdom . |
| 2138838 | 10/1984 | United Kingdom . |

OTHER PUBLICATIONS

E. Kleinpeter et al., Liquid-Crystalline Behaviour of 2,5-Disubstituted 1,3-Dioxanes Subject to the Flexibility of Terminal chains, Tetrahedron, vol. 44 6, pp. 1609-1612 (1988).

*Primary Examiner*—Robert L. Stoll
*Assistant Examiner*—C. Harris
*Attorney, Agent, or Firm*—Blum, Kaplan

[57] ABSTRACT

Trans-2-phenyl-5-trans-4'-alkylcyclohexyl-1,3-dioxane derivatives represented by the general formula:

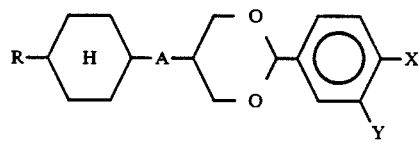

wherein R is a linear alkyl group of 1 to 10 carbon atoms, A is a single covalent bond or a —CH$_2$CH$_2$— group, X is F or CN, Y is F if X is CN or Y is H or F if X is F, and the cyclohexane ring and the 1,3-dioxane ring are trans isomers. The 1,3-dioxane derivatives have large positive dielectric constant anisotropy ($\Delta\epsilon$), small birefringence ($\Delta n$) and have good compatibility with other liquid crystal compounds. The dioxane derivatives may be included in liquid crystal compositions for improved display devices having a low threshold voltage, a low driving voltage and a wide visual angle.

30 Claims, No Drawings

1,3-DIOXANE DERIVATIVES, METHODS OF PREPARATION AND LIQUID CRYSTAL COMPOSITIONS INCLUDING SAME

BACKGROUND OF THE INVENTION

This invention relates to trans-2-fluorophenyl-5-(trans-4'-alkylcyclohexyl)-1,3-dioxane derivatives, and more particularly to novel liquid crystal compositions including trans-2-fluorophenyl-5-(trans-4'-alkylcyclohexyl)-1,3-dioxane derivatives suitable for use in electro-optical displays.

Liquid crystal display devices utilize electro-optical effects possessed by liquid crystals. The liquid crystal materials used in these devices have a nematic phase, a cholesteric phase and a smectic phase. The most widely used display mode uses liquid crystal materials in the nematic phase and includes the dynamic scattering type (DSM), guest-host type (G—H), twisted nematic type (TN), super-twisted nematic type (STN), super-twisted birefringence (SBE) modes and the like. The driving systems used for these liquid crystal display devices include the static driving system, time-sharing driving system (dynamic driving system), active matrix driving system, two frequency driving system and the like.

Liquid crystal display devices have several advantages, particularly when compared with conventional light emission type displays including LED devices, EL devices and CRT devices. The devices are small in size and can be made thin, the devices can be driven at low voltage with low power consumption and the devices have good compatibility with LSI and simple driving circuits. Liquid crystal display devices operate with incident light, and their displays are clearly visible even under direct sunlight. In addition, the liquid crystal material is a light receiving element so that when a liquid crystal display is viewed over a long time, eye strain does not occur. In view of these benefits, liquid crystal display technology has been applied to watches, cameras, electronic counters, audio equipment, automobile dashboard indicators, electronic games, telephone equipment, measuring devices, desk-top electronic calculators, and the like. More particularly, liquid crystal display devices have also been utilized recently in other display devices which require high resolution and many pixels.

The predominant liquid crystal display device is a TN type utilizing a time-sharing driving system. However, the maximum number of scanning lines is about 200 and attempts to increase this number have not been completely successful. In order to increase the number of scanning lines, STN mode liquid crystal display devices, SBE mode liquid crystal display devices and TN mode liquid crystal display devices driven by active matrix driving systems have been used. The STN mode is currently utilized in liquid crystal display devices and personal computers and word processors, while TN mode devices driven by active matrix driving systems are predominantly utilized in color televisions. Thus, liquid crystal display devices continue to attract attention as potentially replacing cathode ray tubes. As a result, liquid crystal display devices have been applied in various areas and it is likely that their use will be broadened further.

For practical use, liquid crystal compositions must possess the following characteristics:

1 The liquid crystal materials must be colorless and thermally, optically, electrically and chemically stable;

2. Have a wide nematic temperature range (MR), particularly over the range of normal room temperature;

3. Have a low threshold voltage ($V_{th}$) of the voltage-luminance characteristic (V-$I_0$ characteristic);

4. A small temperature dependence of threshold voltage ($V_{th}$);

5. A steep rise in voltage-light transmittance ($\gamma$);

6. A small V-$I_0$ characteristic dependence on the view angle property ($\alpha$); and 7 Have a rapid electro-optical response speed.

Many liquid crystal materials possess the first of the above-desired properties, however, no one compound satisfies all of the remaining characteristics. Thus, liquid crystal compositions are formed of several different liquid crystal compounds or liquid crystal compositions are obtained by mixing liquid crystal compounds with pseudo liquid crystal compounds to obtain the desired properties. Pseudo liquid crystal compounds are compounds resembling liquid crystal compounds in their molecular formulas, but fail to manifest liquid crystal phases.

It is convenient to mix liquid crystal compounds of the same type. However, liquid crystal compositions having characteristics 1–7 cannot be attained unless liquid crystal compounds of different types are mixed. The liquid crystal compositions used in TN or STN liquid crystal display devices are of the Np type. Since liquid crystal compositions formed solely of compounds of the Np type have inferior qualities, liquid crystal compositions having more desirable characteristics are obtained by mixing compounds of the Np type with compounds of the Nn type. Generally, these liquid crystal compositions include up to twenty compounds, preferably seven to eight compounds.

In general, liquid crystal compositions must have a nematic liquid crystal temperature range (MR) between at least −20° and +60° C. However, if a liquid crystal display device is used outdoors, for example, on an automobile dashboard, the liquid crystal composition used in the liquid crystal display device must have a wider nematic liquid crystal temperature range, preferably between about −40° and +80° C.

In general, liquid crystal compositions are eutectic mixtures in order to lower the lowermost limit of the nematic temperature range as low as possible. The eutectic mixture composition can be obtained from the following formulae:

$$\ln X_K = \frac{\Delta H_K}{R}\left(\frac{1}{T_K} - \frac{1}{T_L}\right)$$

$$\Sigma X_K = 1$$

where $T_L$ is the lowermost limit of the nematic temperature range;

$X_K$ is the mole fraction of component K at $T_L$;

$\Delta H_K$ is the molar heat of fusion at $T_K$; and

R is the gas constant.

The values provided by the above formulae are relatively close to the actual values if the components are of the same type. However, values provided by the above formulae are inapplicable when the components of the liquid crystal composition are of different type. Thus, personal knowledge is heavily relied upon in formulating liquid crystal compositions.

The upper limit ($T_u$) of the nematic temperature range (MR) can be determined from the following formula:

$$T_U = \Sigma X_K T_{N-I,K}$$

where $T_{N-I,K}$ is the nematic phase-isotropic phase transition temperature (N-I Point) of component K. Generally, the value of $I_U$ obtained using the above formula is higher than the actual value.

The components of a liquid crystal composition are classified by their phase transition point into three different types: (1) low-temperature liquid crystal compounds, (2) intermediate-temperature liquid crystal compounds, and (3) high-temperature liquid crystal compounds. Generally, to obtain a liquid crystal composition having the required characteristics described above, liquid crystal compounds of each of the three types are combined. Low-temperature liquid crystal compounds have crystal-nematic phase transition points (C-N points) or smectic-nematic phase transition points (S-N points) below about 50° C. and N-I points between about 50° and 70° C. The low-temperature liquid crystal compounds are principal components of liquid crystal compositions and determine $T_L$. Examples of low-temperature liquid crystal compounds include compounds having the following formulae:

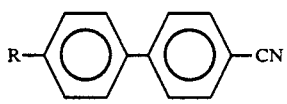

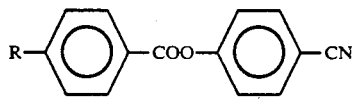

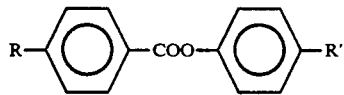

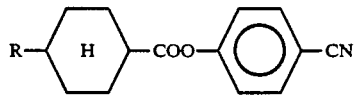

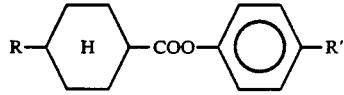

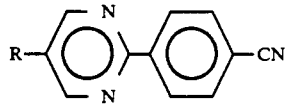

-continued

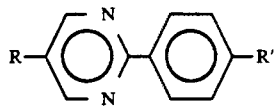

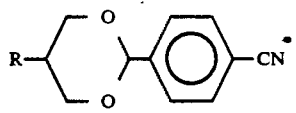

wherein R and R' are linear alkyl or alkoxy groups.

Intermediate-temperature liquid crystal compounds have C-N points between about 50° and 100° C. and N-I points between about 100° and 200° C. and may be principal components of liquid crystal compositions. Examples of intermediate-temperature liquid crystal compounds include compounds having the following formulae:

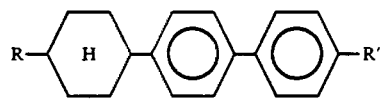

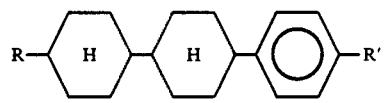

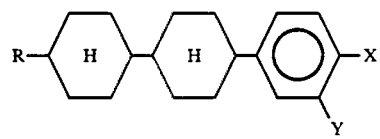

wherein R and R' are linear alkyl or alkoxy groups and X and Y are H or F.

High temperature liquid crystal compounds have C-N points between about 80° and 150° C. and N-I points above about 200° C. and are highly effective in raising the $T_U$ values of liquid crystal compositions. However, high-temperature liquid crystal compounds are disadvantageous since they have high molecular weights and high viscosity. These compounds also do not have good compatibility. Thus, they cannot be added in large amounts. The compounds which have a smectic phase below the nematic phase may be added in relatively larger amounts without incurring compatibility problems. Examples of such high-temperature liquid crystal compounds include compounds having the following formulae:

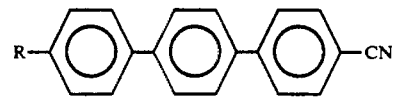

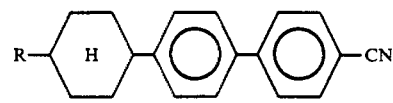

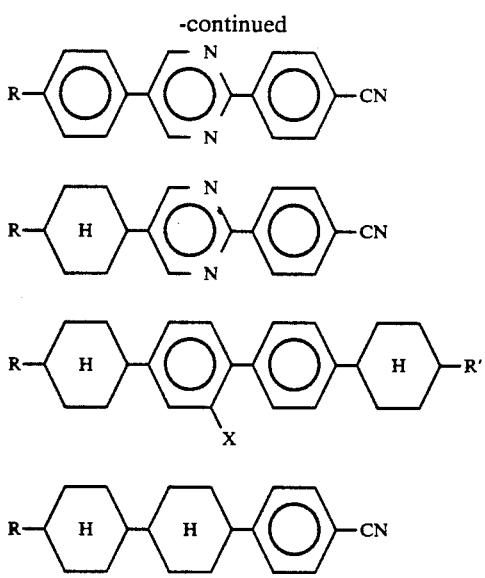

wherein R and R' are linear alkyl or alkoxy groups and X is H or F.

Generally, to prepare a liquid crystal composition having the required characteristics, liquid crystal compounds of each of the three types described above are combined.

In order to lower the driving voltage of a liquid crystal display device, it is necessary to reduce the threshold voltage. However, for a TN type liquid crystal display device, the following relationship exists between the threshold voltage ($V_{th}$), the thickness of the liquid crystal layer (d), the spray elasticity constant ($K_{11}$), the twist elasticity constant ($K_{22}$), the bend elasticity constant ($K_{33}$), dielectric constant anisotropy ($\Delta\epsilon$) and the dielectric constant in a vacuum ($\epsilon_0$):

$$V_{th} = \frac{\pi}{d} \sqrt{\frac{K_{11} + (K_{33} - 2K_{22})/4}{\epsilon_0 \Delta\epsilon}}$$

Thus, in order to lower $V_{th}$, a liquid crystal compound having a large, positive dielectric constant anisotropy ($\Delta\epsilon$) and a small elasticity constant is required. Conventional liquid crystal compounds possessing these characteristics include:

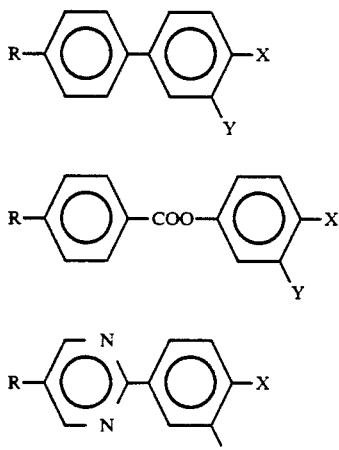

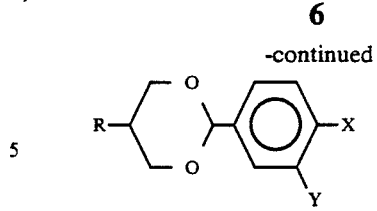

wherein R is a linear alkyl group, X is F or CN, and Y is H or F.

Generally, $V_{th}$ is reduced proportionately with an increase in temperature and this decrease is steep, particularly, near the N-I point. This is due to the dependence of the elasticity constant on temperature. The dependence of the elastic constant of the liquid crystal composition on temperature is lower for the liquid crystal compounds of the Nn type than for those of the Np type. Thus, the addition of an Nn type liquid crystal compound is effective in reducing the dependency of $V_{th}$ on temperature. The dependency of $V_{th}$ on temperature may also be reduced by adding a high-temperature liquid crystal compound. However, the addition of a high-temperature liquid crystal compound would increase the $V_{th}$ of the resulting composition.

The following relationship exists between steepness ($\gamma$), threshold voltage ($V_{th}$) and saturation voltage ($V_{sat}$)

$$\gamma = \frac{V_{sat}}{V_{th}}$$

Generally, $V_{th}$ is the voltage at 10% luminance and $V_{sat}$ is the voltage at 90% luminance. Although the value $\gamma = 1$ is ideal, the value of $\gamma$ is generally between about 1.3 and 1.5 and it is difficult to develop a liquid crystal compound having a lower value of $\gamma$. Steepness ($\gamma$) is related to $K_{33}/K_{11}$, and steepness decreases proportionally as the ratio $K_{33}/K_{11}$ decreases for TN liquid crystal display devices. Pyrimidine compounds, in general, have small $\gamma$ values.

The dependence of the V-$I_0$ characteristic of a TN type liquid crystal display device on the visual angle is due to the pretilt which occurs between the oriented plane and the liquid crystal material. Pretilt is a problem unique to TN type liquid crystal display devices and can be reduced by decreasing the thickness (d) of the liquid crystal layer or by decreasing the birefringence ($\Delta n$) of the liquid crystal composition.

For TN type liquid crystal display devices, transmittance (T), in the absence of an electric field, is expressed by the following formula:

$$T = \sin^2\left(\frac{\pi}{2} \sqrt{1 + u^2}\right)/(1 + u^2)$$

where u is represented by the following formula:

$$u = 2d\Delta n/\lambda$$

In the above formula, T=0 when u≈2, 4, 6, ... The dependency of the V-$I_0$ characteristic on visual angle is smallest when u 2. Due to the difficulty of forming a liquid crystal composition having a small value of $\Delta n$, previously the only method of reducing the dependency of V-$I_0$ on visual angle has been to decrease the value of d. However, current manufacturing techniques permit no appreciable decrease in the value of d. Thus, liquid crystal cells are manufactured with values of d and Δn so that u≃4. Accordingly, the development of liquid crystal compounds having small Δn values would result in the formation of a TN type liquid crystal cell having a dependency of V-$I_0$ on visual angle low enough to satisfy the equation u≃2.

The initiating speed $\tau_{ON}$ and the trailing speed, $\tau_{OFF}$, which are measures of the response speed of a twisted nematic liquid crystal display device may be calculated by the following formulae:

$$\tau_{ON} = \eta d^2/(\epsilon_0 \Delta \epsilon V^2 - \pi^2 K)$$

$$\tau_{OFF} = \eta d^2/K\pi^2$$

where
η is the viscosity;
V is the applied voltage; and
K is represented by the following formula:

$$K = K_{11} + (K_{33} - 2K_{22})/4$$

Thus, a high speed response is obtained by decreasing the thickness (d) of the liquid crystal layer, lowering the viscosity (η) of the liquid crystal material and raising the value of the elasticity constant (K). From the perspective of the liquid crystal material, the response speed may be raised by using a material having as small a value of η/K as possible. Compounds having small η/K values are generally known as viscosity decreasing agents and include compounds having the following formulae:

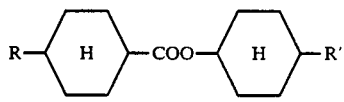

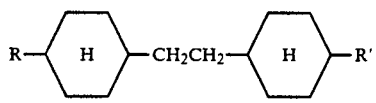

wherein R and R' are linear alkyl or alkoxy groups.

In a liquid crystal display device having a time sharing driving system, the relationship between the steepness (γ) and the maximum allowable number of scanning lines (N) is expressed by the following formula:

$$N = \left(\frac{\gamma^2 + 1}{\gamma^2 - 1}\right)^2$$

From the above formula, it is evident that the value of N increases proportionately as the value of γ approximates 1. Generally, when a time sharing driving system is used in a liquid crystal display device, the voltage margin (M) is used to evaluate the effectiveness of a given liquid crystal composition used as the liquid crystal material. The voltage margin (M) is defined by the following formula:

$$M = \frac{V_{th}(T = 40°\,C., \phi = 40°\,C.) - V_{sat}(T = 0°\,C., \phi = 10°)}{V_{th}(T = 40°\,C., \phi = 40°\,C.) + V_{sat}(T = 0°\,C., \phi = 10°\,C.)} \times 100$$

wherein $V_{th}$ and $V_{sat}$ are the voltage at 10% and 50% of light transmittance, respectively; T is the temperature; and φ is the visual angle (with the front side 0°).

The above formula shows that three characteristics are important to obtain a large-scale time-sharing driving system:

(1) The steepness (γ) should be sharp.

(2) The dependence of $V_{th}$ and $V_{sat}$ on temperature should be small.

(3) The dependence on visual angle (α) should be small.

Compounds having the following formulae are known to have the above desired characteristics:

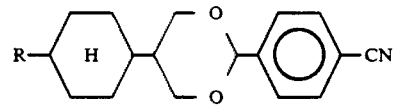

[H-M Vorbrodt, et. al., Mol. Cryst. Liq. Cryst., 123, 137 (1985)]

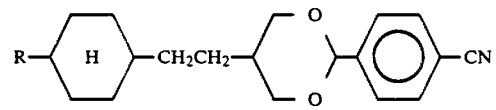

[E. Kleinpeter, et. al., Tetrahedron, 44, 1809 1988)]

Although the above nematic liquid crystal compounds have high N-I points and small values of Δn and γ, they do not have good compatibility with conventional liquid crystal compositions.

Accordingly, it is desirable to provide a nematic liquid crystal material and compositions having large positive Δε and small Δn, which have good compatibility with other liquid crystal compounds, and which may be used in a large-scale time sharing driving system at low voltage.

SUMMARY OF THE INVENTION

Generally speaking, in accordance with the invention, trans-2-fluorophenyl-5-(trans-4'-alkylcyclohexyl)-1,3-dioxane derivatives represented by the general formula:

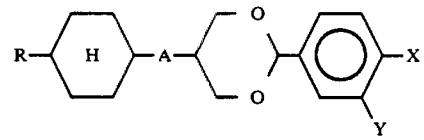

wherein R is a linear alkyl group having from 1 to 10 carbon atoms, A is a single covalent bond or a —CH$_2$CH$_2$— group, X is F or CN, Y is F when X is CN and Y is H or F when X is F, the cyclohexane ring and the 1,3-dioxane ring are the trans isomers and the compounds exhibit the nematic phase are provided. The trans-2-fluorophenyl-5-(trans-4'-alkylcyclohexyl)-1,3-dioxane derivatives have high nematic phase-isotropic liquid phase transition temperatures (N-1 Points), large positive dielectric constant anisotropy (Δε) and small birefringence (Δn). The trans-2-fluorophenyl-5-(trans-4'-alkylcyclohexyl)-1,3-dioxane derivatives may be mixed with other liquid crystal compounds to obtain liquid crystal display devices having a wide temperature range, low threshold voltage, a wide visual angle and are capable of large-scale time-sharing driving at low voltage.

Accordingly, it is an object of the invention to provide an improved liquid crystal compound.

It is another object of the invention to provide trans-2-fluorophenyl-5-(trans-4'-alkylcyclohexyl)-1,3-dioxanederivatives.

It is a further object of the invention to provide trans-2-fluorophenyl-5-(trans-4'-alkylcyclohexyl)-1,3-dioxane derivatives having high N-I Points, large positive dielectric constant anisotropy (Δε) and small birefringence (Δn).

Still another object of the invention is to provide trans-2-fluorophenyl-5-(trans-4'-alkylcyclohexyl)-1,3-dioxane derivatives suitable for use in liquid crystal compositions for electro-optical display devices.

Still a further object of the invention is to provide improved liquid crystal compositions including trans-2-fluorophenyl-5-(trans-4'-alkylcyclohexyl)-1,3-dioxane derivatives for improving the temperature range and visual angle and lowering the driving voltage.

Yet a further object of the invention is to provide a method for preparing improved trans-2-fluorophenyl-5-(trans-4'-alkylcyclohexyl)-1,3-dioxane derivatives.

Yet another object of the invention is to provide improved liquid crystal display devices including the liquid crystal compositions including trans-2-fluorophenyl-5-(trans-4'-alkylcyclohexyl)-1,3-dioxane derivatives.

Still other objects and advantages of the invention will in part be obvious and will in part be apparent from the specification.

The invention accordingly comprises the several steps and the relation of one or more of such steps with respect to each of the others thereof, which will be exemplified in the composition, method and device hereinafter disclosed, and the scope of the invention will be indicated in the claims.

DESCRIPTION OF THE PREFERRED EMBODIMENTS

The liquid crystal compound dance with the invention are trans-2-fluorophenyl-5-(trans-4'-alkylcyclohexyl)-1,3-dioxane derivatives represented by the general formula as follows:

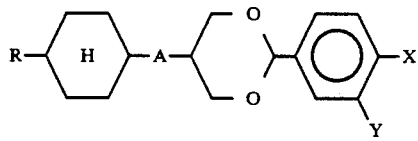

wherein R is a linear alkyl group having from 1 to 10 carbon atoms, A is a single covalent bond or a —CH$_2$CH$_2$— group, X is F or CN, Y is F when X is CN, Y is H or F when X is F, the cyclohexane ring and the 1,3-dioxane ring are the trans isomers and the compounds exhibit the nematic phase.

The trans-2-fluorophenyl-5-(trans-4'-alkylcyclohexyl)-1,3-dioxane compounds of this invention represented by the following general formulae II to VII have relatively high nematic phase-isotropic liquid phase transition points (N-I points), large positive dielectric anisotropy (Δε) and small birefringence (Δn).

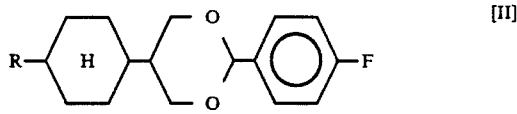

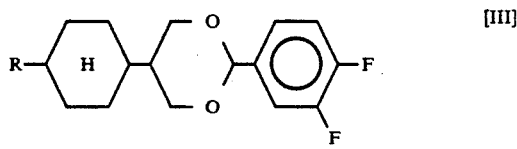

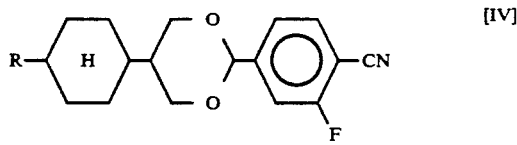

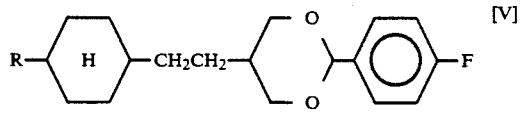

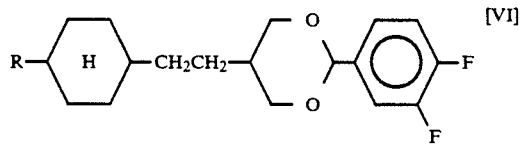

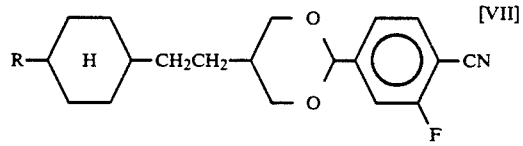

When the 1,3-dioxane derivatives prepared in accordance with the invention are mixed with conventional liquid crystal compounds or with analogues thereof, the resulting compositions have a wide nematic liquid crystal temperature range (MR), a low threshold voltage, a wide visual angle and the compositions permit large scale time shared driving at a low voltage. In general, the 1,3-dioxane derivatives can be included in a conventional liquid crystal composition from about to 50% by weight, preferably between about 3 and 30% by weight to avoid compatibility problems. One or more 1,3-dioxane derivative may be included in a conventional liquid crystal composition. Preferably, at least two trans-2-fluorophenyl-5-(trans-4'-alkylcyclohexyl-1,3-dioxane derivatives are included to improve characteristics (2) through (6) described above.

The trans-2-fluorophenyl-5-(trans-4'-alkylcyclohexyl-1,3-dioxane derivatives in accordance with the invention eliminate the compatibility problems associated with the following types of compounds:

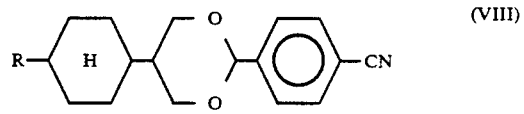

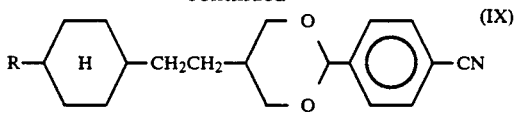

The phase transition points of compounds II to IX wherein R is $C_4H_9$ are shown in Table 1.

TABLE 1

| | C . | S . | N . | I |
|---|---|---|---|---|
| II | 70.0° C. | (77.7° C.) | 145.0° C. | |
| III | 89.8° C. | — | 109.7° C. | |
| IV | 89.6° C. | — | 174.1° C. | |
| V | 95.6° C. | — | 119.4° C. | |
| VI | 83.0° C. | — | 87.0° C. | |
| VII | 63.5° C. | — | 142.8° C. | |
| VIII | 74.6° C. | 91.5° C. | 221.2° C. | |
| IX | 72.2° C. | 91.7° C. | 179.4° C. | |

Table 1 shows that conventional compounds VIII and IX, which have a cyano group at the 4 position of the phenyl group have the highest N-I points, followed by the compounds IV and VII having a cyano group at the 4 position and a fluoro group at the 3 position of the phenyl group. Compounds II and V having a fluoro group at the 4 position, and compounds III and VI having fluoro groups at the 3 and 4 positions of the phenyl group have the lowest N-I points.

The dioxane derivatives with cyano groups at the 4 position of the phenyl group, compounds VIII and IX, have the highest C-N points, followed by the compounds III and IV having fluoro groups at the 3 and 4 positions of the phenyl group. Compounds II and V having fluoro groups at the 4 position, and compounds IV and VII having a fluoro group at the 3 position and a cyano group at the 4 position of the phenyl group have the lowest C-N points. When compounds II through IX are classified as low temperature, intermediate temperature or high temperature liquid crystal compounds, compound VIII is the only compound labelled as a high temperature liquid crystal compound. Compounds II–VII and IX are labelled as intermediate temperature liquid crystal compounds.

Compounds II–IX have been tested for compatibility with other liquid crystal compositions. The results are shown in Table 4 described in Composition Example 1. Compounds II–VII, the dioxane derivatives in accordance with the invention, have improved compatibility with liquid crystal compositions over compounds VIII and IX. If an intermediate-temperature liquid crystal compound has sufficient compatibility, it can be used as the main component of a liquid crystal composition. Thus, the 1,3-dioxane derivatives in accordance with the invention can be used as main components of liquid crystal compositions.

In general, the trans-2-fluorophenyl-5-(trans-4'-alkylcyclohexyl-1,3-dioxane derivatives can be included in a conventional liquid crystal composition from about 1 to 50% by weight, preferably from about 3 to 30% to avoid compatibility problems. If the dioxane derivatives are included in a liquid crystal composition at less than about 3 by weight, the advantages of the dioxane derivatives are not conspicuously manifested in the resultant mixtures.

The 1,3-dioxane derivatives prepared in accordance with the invention are compatible with many liquid crystal materials, including the compounds described in Composition Examples 1–8 and the following:

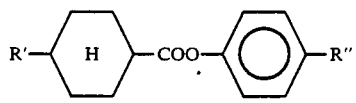
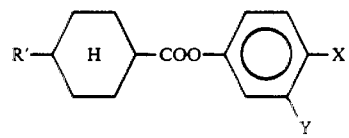
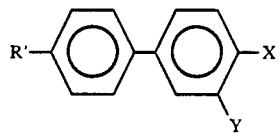
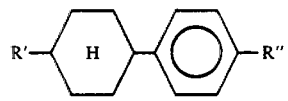
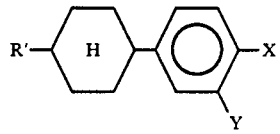
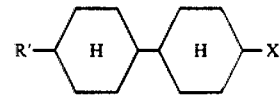
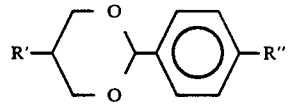
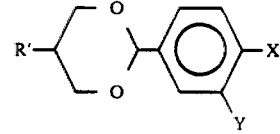
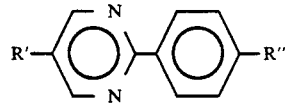
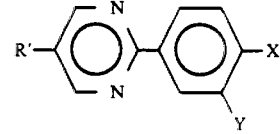

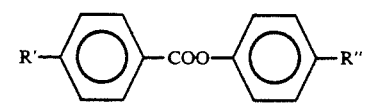
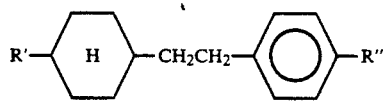
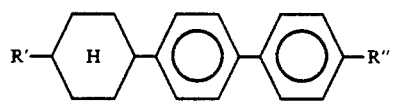
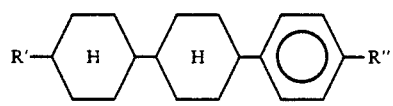
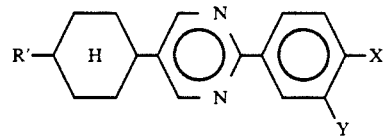
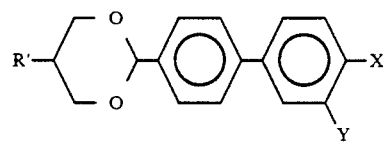
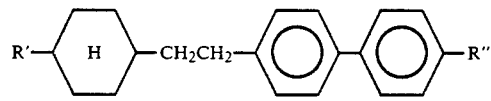
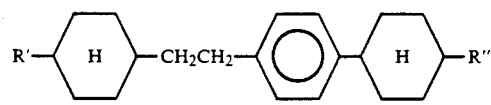
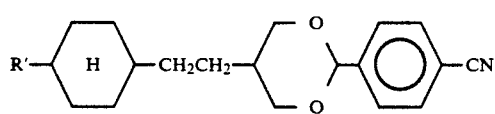
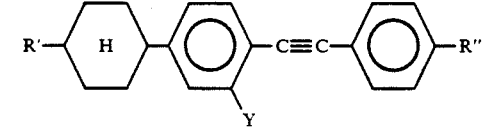
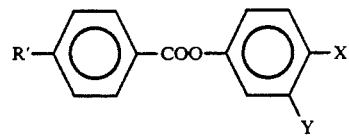
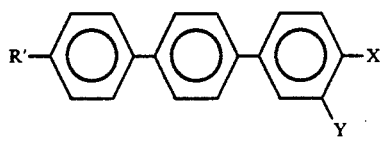
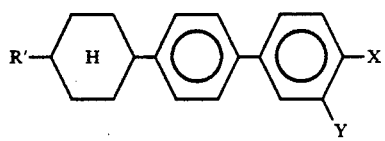
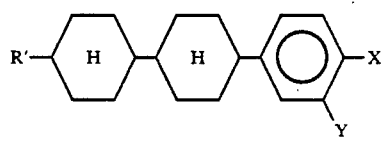
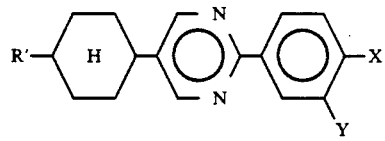
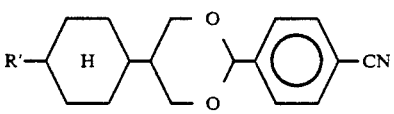
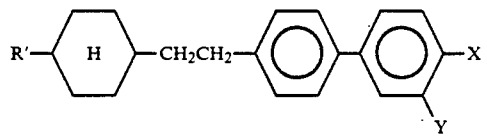
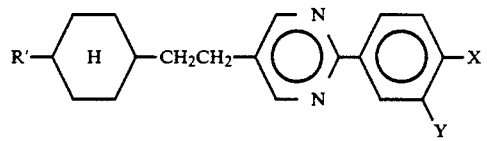
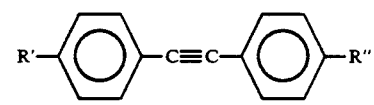
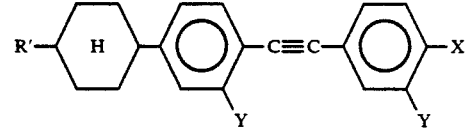
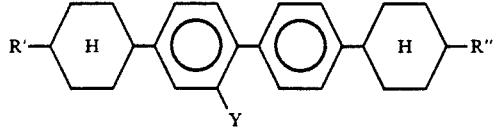

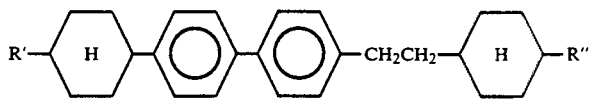

wherein R and R" are linear alkyl, linear alkoxy, linear alkenyl, or linear alkenyloxy groups, X is CN or F, and Y is H or F. The compounds listed above represent only a small number of the compounds that the dioxane derivatives of the invention are compatible with. The threshold voltage ($V_{th}$) and the dependence of $V_{th}$ on temperature ($\Delta T$) over the temperature range of 0° to 40° C. of liquid crystal compositions formed by including 10% by weight of each of compounds II-VII, wherein R is $-C_4H_9$ and conventional compounds VIII-IX,

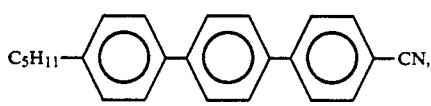

and

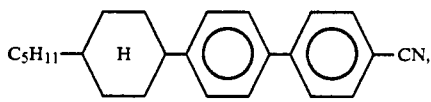

in 90% by weight of ZLI-1565 are shown in Table 2.

TABLE 2

| Compound | [II] | [III] | [IV] | [V] | [VI] | [VII] | [VIII] | [IX] | [X] | [XI] |
|---|---|---|---|---|---|---|---|---|---|---|
| $V_{th}$ (V) | 2.51 | 2.42 | 2.19 | 2.50 | 2.38 | 2.23 | 2.38 | 2.45 | 2.51 | 2.47 |
| $\Delta T$ (−V) | .28 | 0.30 | 0.31 | 0.25 | 0.31 | 2.32 | 0.31 | 0.31 | 0.29 | 0.29 |

As shown in Table 2, compounds II and V having substituted at the 4-position of the phenyl group in 90% ZLI-1565 have a $V_{th}$ equal to compound X. Compounds III and VI, having F substituted at the 3 and 4 positions, have a $V_{th}$ equal to conventional compounds VIII-XI, having CN substituted at the 4-position. Compounds IV and VII, having F substituted at the 3 position and CN substituted at the 4 position of the phenyl group, have considerably lower $V_{th}$. Thus, compounds IV and VII are effective in lowering the threshold voltage of liquid crystal compositions and, consequently, are useful in preparing a large scale time sharing driving system which operates at low voltage.

Compounds III and VI, although inferior to conventional compounds VIII and IX with regard to N-I points, exhibit an equal effect in lowering $V_{th}$, have lower $\Delta n$ than conventional compounds VIII and IX and have good compatibility. Thus, they have a wider range of utility than compounds VIII and IX.

Compounds II and V, having F substituted at the 4 position of the phenyl group, have particularly small dependence of $V_{th}$ on temperature ($\Delta T$). Compounds III, IV, VI and VII have substantially the same dependence of $V_{th}$ on temperature. Since compounds II and V have relatively high N-I points and small $\Delta n$ values, they are extremely useful for large scale time sharing driving systems.

With respect to steepness ($\gamma$), compounds II-VII have magnitudes of $\gamma$ which are equal to those of conventional compounds VIII and IX. Thus, they are not particularly notable.

The $\Delta n$ values for the compositions including compounds II-VII and conventional compounds VIII-XI described with regard to Table 2 ar shown in Table 3.

TABLE 3

| Compound | [II] | [III] | [IV] | [V] | [VI] | [VII] | [VIII] | [IX] | [X] | [XI] |
|---|---|---|---|---|---|---|---|---|---|---|
| $\Delta n$ | 0.124 | 0.123 | 0.130 | 0.124 | 0.123 | 0.127 | 0.130 | 0.128 | 0.149 | 0.139 |

As shown in Table 3, compounds having a large number of benzene rings and having CN substituted at the 4 position of the phenyl group, yield compositions having large values of $\Delta n$. Compounds II, III, V and VI, having F as a substituent, have small $\Delta n$ values. Due to these small values of $\Delta n$, compounds II, III, V and VI permit the production of liquid crystal cells satisfying the equation $U \simeq 2$ without requiring the thickness of the liquid crystal layer (d) to be decreased by a large amount. These compounds also permit production of liquid crystal devices having a wide visual angle and they are useful components in large scale time sharing driving systems.

With regard to responsivity, 1,3-dioxane derivatives do not have particularly high viscosity or low elastic constants when compared with other tricyclic liquid crystal compounds. However, the 1,3-dioxane derivatives have high response speeds because liquid crystal cells adapted to satisfy $U \simeq 2$ have low values of cell thickness (d). Theoretically, the response speed is inversely proportional to the square of thickness (d) of the cell. (In actuality, the response speed is inversely proportional to thickness (d) to the 1.5 power.) Thus, a decrease in the thickness (d) of the liquid crystal cell is more effective than improving the ratio $\eta/K$, of the liquid crystal material.

Four properties are necessary for time shared driving: large $\gamma$, low $V_{th}$, small $\Delta T$ and low $\alpha$. Compounds II-VII have values of $\gamma$ equal to those of conventional compounds. Compounds II and V have a low dependence of $V_{th}$ on temperature. Compounds II, III, V and VI have low values of $\alpha$. Finally, compounds VI and VII lower the driving voltage.

When one compound selected from compounds II-VII is mixed with a conventional liquid crystal composition, a liquid crystal composition capable of being driven with large scale time share driving results. However, when a mixture of between about 2 and 6 compounds selected from compounds II-VII is mixed with a conventional liquid composition, improved liquid crystal compositions are formed. In particular, when compound IV or VII is added to the mixture, a liquid crystal composition which reduces the pressure resistance of LSI, and is extremely suitable for large scale time share driving, results.

In summary, the trans-2-fluorophenyl-5-(trans-4'-alkylcyclohexyl-1,3-dioxane derivatives compounds II-VII, are suitable for use in large scale time share driving systems. Thus, the liquid crystal compositions formed by incorporating one or more of compounds II-VII are suitable for large scale time share driving at low voltage. Additionally compounds II-VII have good compatibility and are thoroughly miscible with all liquid crystal compounds. The trans-2-fluorophenyl-5-(trans-4'-alkylcyclohexyl-1,3-dioxane derivatives may be included up to 50 weight percent in a liquid crystal composition, preferably between about 3 and 30 weight percent.

The trans-2-fluorophenyl-5-(trans-4'-alkylcyclohexyl-1,3-dioxane derivatives wherein A is a single covalent bond, X is F and Y is H can be produced following Reaction Scheme I:

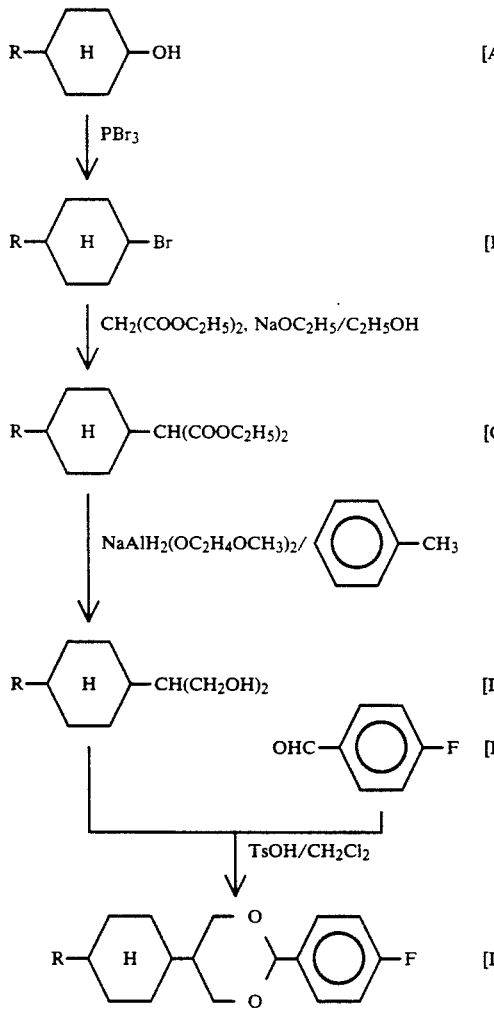

Compound [A], a 4-alkylcyclohexanol is brominated with phosphorus tribromide ($PBr_3$) to yield compound [B], a cis-trans mixture of 4-alkyl-1-bromocyclohexane. Compound [B] is used as a cis-trans mixture or a trans compound. If a $HBr$—$H_2SO_4$ system is used, the reaction results in a poor yield of compound [B] due to large amounts of 4-alkylcyclohexene produced as a by-product.

Compound [B] is reacted with diethyl malonate in anhydrous ethanol in the presence of sodium ethoxide ($NaOC_2H_5$) to yield compound [C], a diethyl-4-alkylcyclohexyl malonate. The yield of compound [C] is low due to the formation of 4-alkylcyclohexene, a by-product of the reaction.

Compound [C] is reduced with sodium bis(methoxyethoxy) aluminum hydride ($NaAlH_2(OC_2H_4OCH_3)_2$) in toluene to yield compound [D] a 2-(4-alkylcyclohexyl) propane-1,3-diol (cis-trans mixture).

Compound [D] and compound [E], 4-fluorobenzaldehyde, are reacted and the product of the reaction is dehydrated in dichloromethane in the presence of p-toluene sulfonic acid (TsOH), used as a catalyst, to yield a 2-(4'-fluorophenyl)-5-(4'-alkylcyclohexyl)-1,3-dioxane. The cyclohexane ring and the 1,3-dioxane ring are both cis-trans mixtures. The cis-trans mixture is recrystallized and the trans-trans moiety is separated out to yield compound [II], a novel liquid crystal compound in accordance with the invention.

The trans-2-fluorophenyl-5-(trans-4'-alkylcyclohexyl-1,3-dioxane derivatives wherein A is a single covalent bond and X and Y and F can be produced by the following Reaction Scheme II:

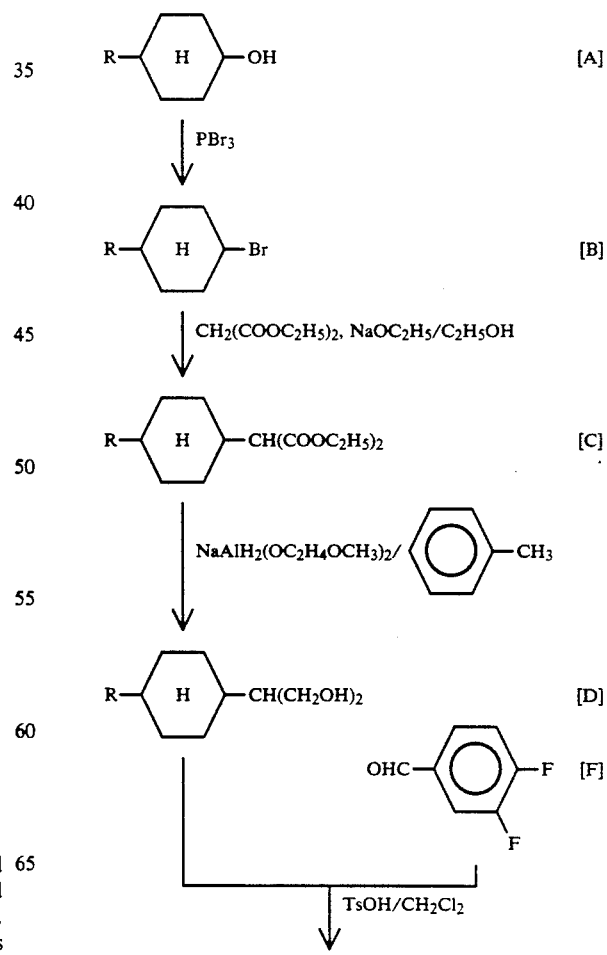

-continued
REACTION SCHEME II

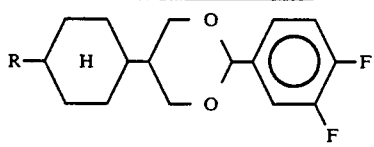
[III]

Compound [A], a 4-alkylcyclohexanol is brominated with phosphorus tribromide (PBr₃) to yield compound [B], a cis-trans mixture of 4-alkyl-1-bromocyclohexane. Compound [B] is used as a cis-trans mixture or a trans compound. If a HBr—H₂SO₄ system is used, the reaction results in a poor yield of compound [B] due to large amounts of 4-alkylcyclohexene produced as a by-product.

Compound [B] is reacted with diethyl malonate in anhydrous ethanol in the presence of sodium ethoxide (NaOC₂H₅) to yield compound [C], a diethyl-4-alkylcyclohexyl malonate. The yield of compound [C] is low due to the formation of 4-alkylcyclohexene, a by-product of the reaction.

Compound [C] is reduced with sodium bis(methoxyethoxy) aluminum hydride (NaAlH₂(OC₂H₄OCH₃)₂) in toluene to yield compound [D], a 2-(4'-alkylcyclohexyl) propane-1,3-diol (cis-trans mixture).

In dichloromethane, in the presence of TsOH, acting as a catalyst, compound [D] is reacted with compound [F], a commercially available 3,4-difluorobenzaldehyde, to yield a 2-(3',4'-difluorophenyl)-5-(4'-alkyclyclohexyl)-1,3-dioxane. The cyclohexane ring and the 1,3-dioxane ring are both cis-trans mixtures. The cis-trans mixture is recrystallized and the trans-trans moiety is separated out to yield compound [III], a novel liquid crystal compound in accordance with the invention.

The trans-2-fluorophenyl-5-(trans-4'-alkylcyclohexyl-1,3-dioxane derivatives wherein A is a single covalent bond, X is CN and Y is F can be produced by the following Reaction Scheme III:

REACTION SCHEME III

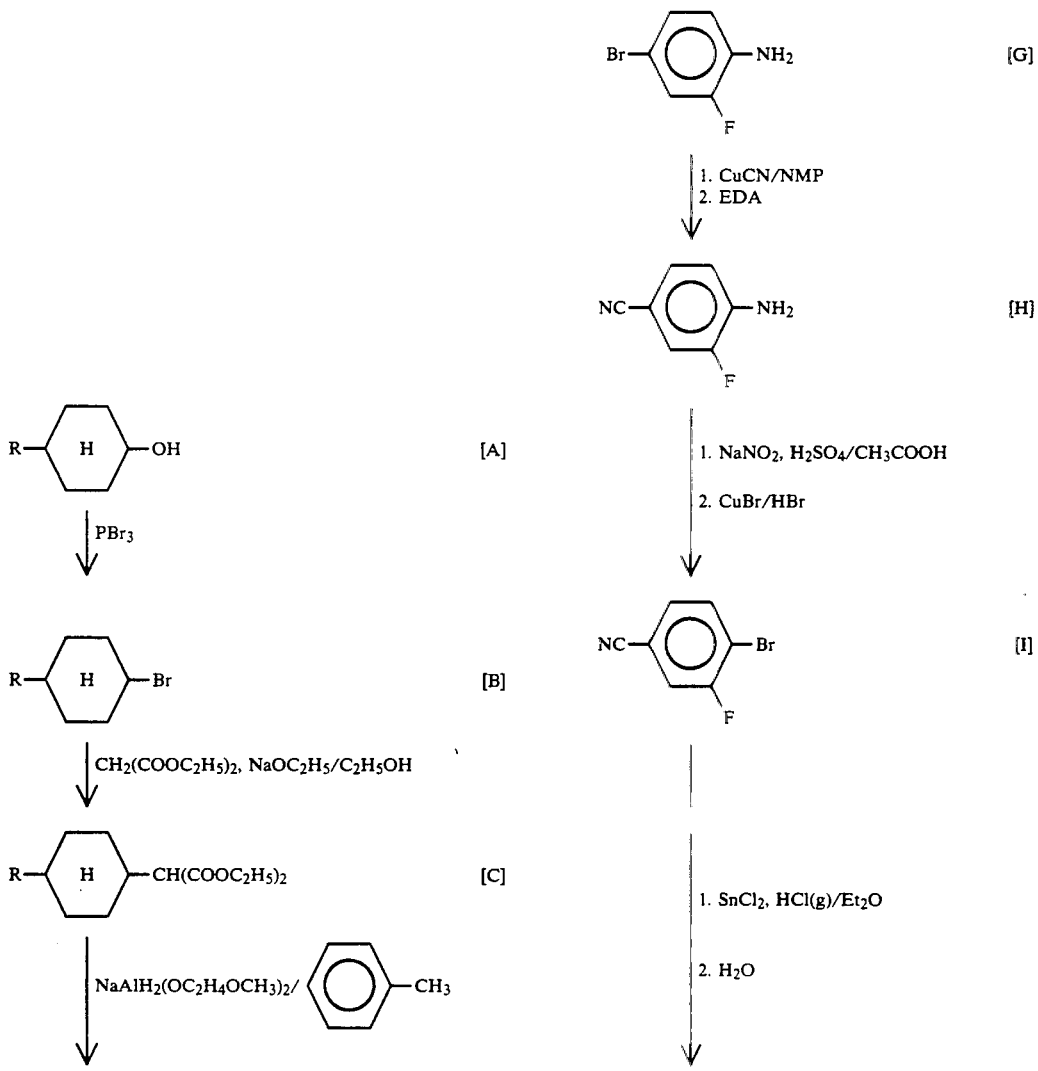

-continued
REACTION SCHEME III

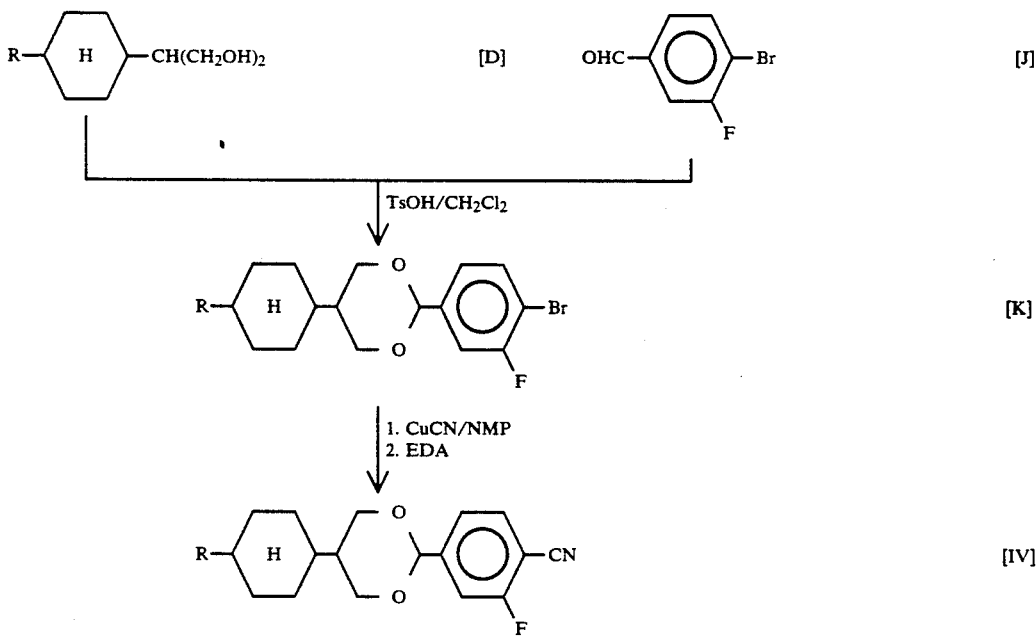

Compound [A], a 4-alkylcyclohexanol is brominated with phosphorus tribromide (PBr₃) to yield compound [B], a cis-trans mixture 4-alkyl-1-bromocyclohexane. Compound [B] is used as a cis-trans mixture or a trans compound. If a HBr—H₂SO₄ system is used, the reaction results in a poor yield of compound [B] due to large amounts of 4-alkylcyclohexene produced as a by-product.

Compound [B] is reacted with diethyl malonate in anhydrous ethanol in the presence of sodium ethoxide (NaOC₂H₅) to yield compound [C], a diethyl-4-alkylcyclohexyl malonate. The yield of compound [C] is low due to the formation of 4-alkylcyclohexene, a by-product of the reaction.

Compound [C] is reduced with sodium bis(methoxyethoxy) aluminum hydride (NaAlH₂(OC₂H₄OCH₃)₂) in toluene to yield compound [D], a 2-(4'-alkylcyclohexyl) propane-1,3-diol (cis-trans mixture).

In N-methyl-2-pyrrolidinone (NMP), compound [G], a commercially available 4-bromo-2-fluoroaniline (manufactured by Aldrich) is cyanated with copper (I) cyanide to form a copper complex. The copper complex is decomposed with ethylene diamine (EDA) to yield compound [H], a 4-amino-3-fluorobenzonitrile. Alternatively, a solution of iron (III) chloride in hydrochloric acid may be used to decompose the copper complex.

In glacial acetic acid, compound [H] is diazodized with nitrocil hydrogen sulfate (HSO₄—ONO₂) prepared from sodium nitrite (NaNO₂) and concentrated sulfuric acid. The diazonium salt formed is brominated in hydrobromic acid with copper (I) bromide (CuBr) to yield compound [I], 4-bromo-3-fluorobenzonitrile.

In diethyl ether, compound [I] is reacted with tin (II) chloride (SnCl₂), saturated with hydrogen chloride gas, to reduce the cyano group into an aldehyde group and form a tin complex. The tin complex is decomposed with hot water to yield compound [J], 4-bromo-3-fluorobenzaldehyde.

Compound [D] and compound [J] are reacted and the product of the reaction is dehydrated in dichloromethane in the presence of TsOH, used as a catalyst, to yield compound [K], a 2-(4'-bromo-3'-fluorophenyl)-5-(4-alkylcyclohexyl)-1,3-dioxane. In compound [K], the cyclohexane ring and the 1,3-dioxane ring are both cis-trans mixtures.

In NMP, compound [K] is cyanated with CuCN to form a copper complex. The copper complex is decomposed with EDA to yield a 2-(4'-cyano-3'-fluorophenyl)-5-(4,-alkylcyclohexyl)-1,3-dioxane. During the cyanation, some of the 1,3-dioxane rings are isomerized from the trans isomer to the cis isomer. The cis-trans mixture is recrystallized and the trans-trans moiety is separated out to yield compound [IV], a novel liquid crystal compound in accordance with the invention.

The trans-2-fluorophenyl-5-(trans-4'-alkylcyclohexyl-1,3-dioxane derivatives wherein A is a —CH₂CH₂— group, X is F and Y is H can be produced by the following Reaction Scheme IV:

REACTION SCHEME IV

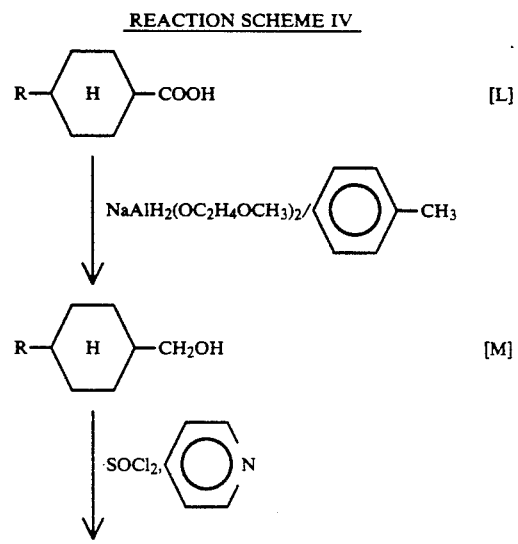

-continued
REACTION SCHEME IV

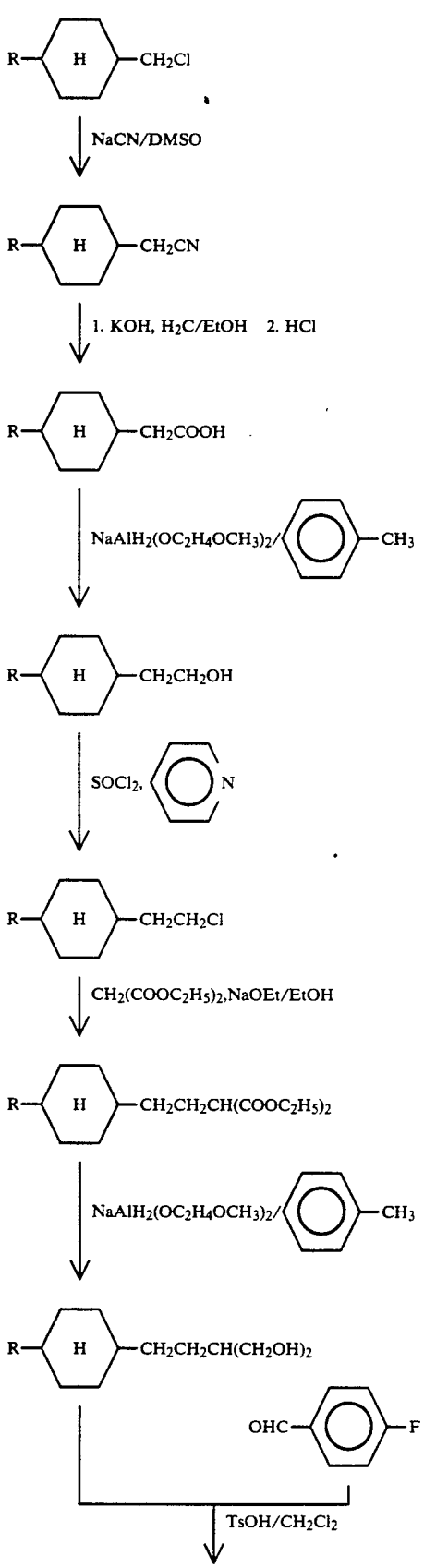

-continued
REACTION SCHEME IV

[V]

In toluene, a compound [L] a trans-4-alkylcyclohexane carboxylic acid is reduced with sodium bis(methoxyethoxy) aluminum hydride ($NaAlH_2(OC_2H_4OCH_3)_2$) to yield a compound [M], a trans-4-alkylcyclohexyl methanol. Alternatively, compound [L] is converted into a trans-4-alkylcyclohexane carbonyl chloride with thionyl chloride ($SOCl_2$) and reduced with ($NaAlH_2(OC_2H_4OCH_3)_2$) to yield compound [M].

In anhydrous pyridine, compound [M] is chlorinated with $SOCl_2$ to yield compound N], a trans-4-alkylcyclohexyl chloromethane. In dimethyl sulfoxide (DMSO), compound [N] is cyanated with sodium cyanide (NaCN) to yield compound [O], a trans-4-alkylcyclohexyl acetonitrile.

In ethanol, compound [O] is hydrolyzed with potassium hydroxide (KOH) to form a hydrolyzate. The hydrolyzate is neutralized with HCl to yield compound [P], a trans-4-alkyl cyclohexyl acetic acid. In toluene, compound [P] is reduced with ($NaAlH_2(OC_2H_4OCH_3)_2$) to yield compound [Q], a 2-(trans-4'-alkylcyclohexyl) ethanol. Alternatively, compound [P] is chlorinated to yield a trans-4-alkylcyclohexylacetyl chloride and the acetyl chloride is reduced with ($NaAlH_2(OC_2H_4OCH_3)_2$).

In anhydrous pyridine, compound [Q] is chlorinated with $SOCl_2$ to yield compound [R], a 2-(trans-4'-alkylcyclohexyl)-1-chloroethane. In anhydrous ethanol, compound [R] is alkylated with diethyl malonate and sodium ethoxide (NaOEt) to yield compound [S], a diethyl 2-(trans-4'-alkylcyclohexyl)ethylmalonate. Compound [S] is obtained in a higher yield if compound [Q] is brominated to yield a 2-(trans-4'-alkylcyclohexyl)-1-bromoethane and the bromoethane is substituted for a compound [R]. In toluene, compound [S] is reduced with ($NaAlH_2(OC_2H_4OCH_3)_2$) to yield compound [T], a 2-[2'-(trans-4''-alkylcyclohexyl)ethyl]propane-1,3-diol.

Compound [T] and compound [E], 4-fluorobenzaldehyde, are reacted and the product of the reaction is dehydrated in dichloromethane, in the presence of TsOH, used as a catalyst, to yield a 2-(4'-fluorophenyl)-5-[2'-(4''-alkylcyclohexyl)ethyl]-1,3-dioxane. The cyclohexane ring and the 1,3-dioxane ring are both cis-trans mixtures. The cis-trans mixture is recrystallized and the trans-trans moiety is separated out to yield compound [V], a novel liquid crystal compound in accordance with the invention.

The trans-2-fluorophenyl-5-(trans-4'-alkylcyclohexyl)-1,3-dioxane derivatives wherein A is a —$CH_2CH_2$— group, X is F and Y is H can be produced by the following Reaction Scheme V:

REACTION SCHEME V

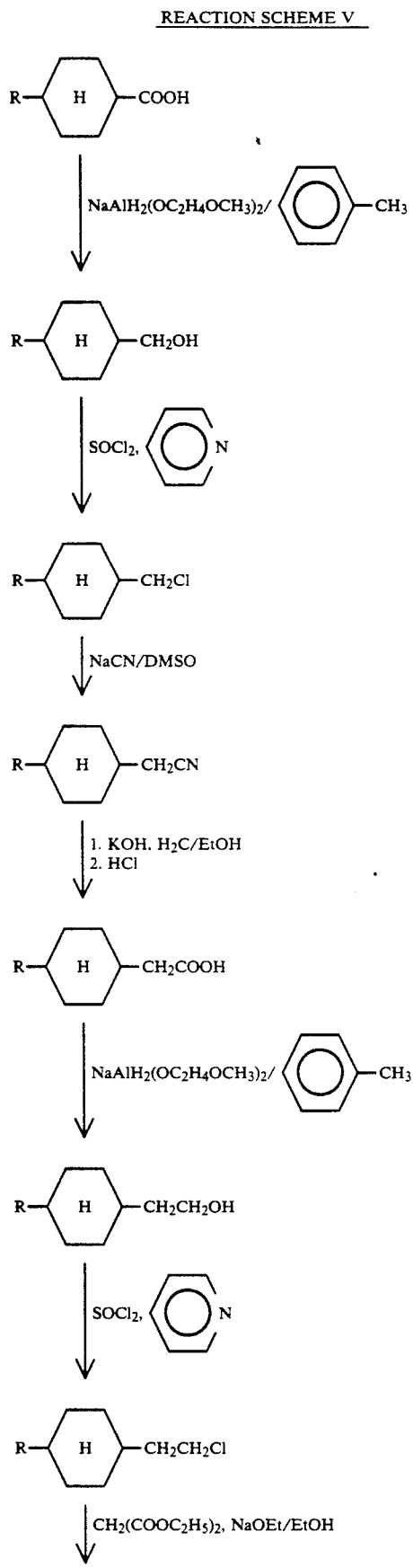

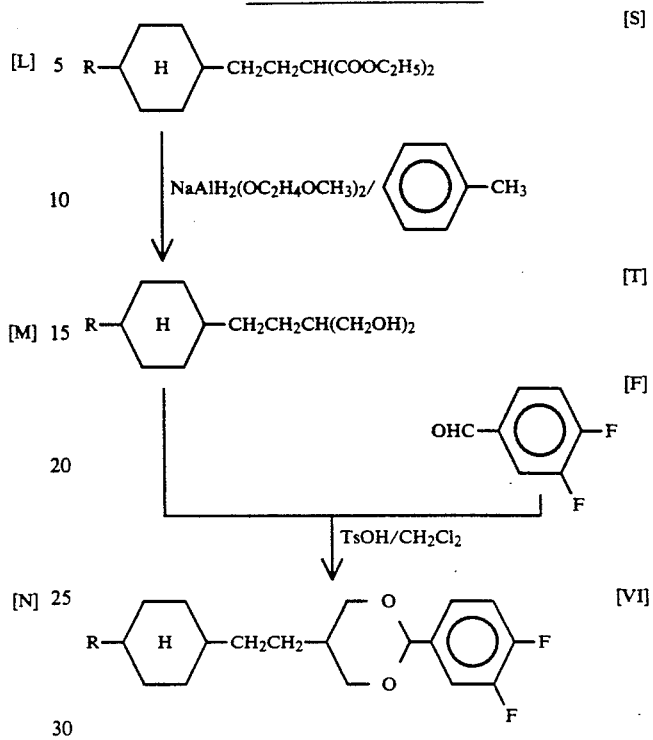

In toluene a compound [L] a trans-4-alkylcyclohexane carboxylic acid is reduced with sodium bis(methoxyethoxy) aluminum hydride (NaAlH$_2$(OC$_2$H$_4$OCH$_3$)$_2$) to yield a compound [M], a trans-4-alkylcyclohexyl methanol. Alternatively, compound [L] is converted into a trans-4-alkylcyclohexane carbonyl chloride with thionyl chloride (SOCl$_2$) and reduced with (NaAlH$_2$(OC$_2$H$_4$OCH$_3$)$_2$ to yield compound [M].

In anhydrous pyridine, compound [M] is chlorinated with SOCl$_2$ to yield compound [N], a trans-4-alkylcyclohexyl chloromethane. In dimethyl sulfoxide (DMSO), compound [N] is cyanated with sodium cyanide (NaCN) to yield compound [O], a trans-4-alkylcyclohexyl acetonitrile.

In ethanol, compound [O] is hydrolyzed with potassium hydroxide (KOH) to form a hydrolyzate. The hydrolyzate is neutralized with HCl to yield compound [P], a trans-4-alkyl cyclohexyl acetic acid. In toluene, compound [P] is reduced with (NaAlH$_2$(OC$_2$H$_4$OCH$_3$)$_2$ to yield compound [Q], a 2-trans-4'-alkylcyclohexyl) ethanol. Alternatively, compound P] is chlorinated to yield a trans-4-alkylcyclohexylacetyl chloride and the acetyl chloride is reduced with (NaAlH$_2$(OC$_2$H$_4$OCH$_3$)$_2$.

In anhydrous pyridine, compound [Q] is chlorinated with SOCl$_2$ to yield compound [R], a 2-(trans-4'-alkylcyclohexyl)-1-chloroethane. In anhydrous ethanol, compound [R] is alkylated with diethyl malonate and sodium ethoxide (NaOEt) to yield compound [S], a diethyl 2-(trans-4'-alkylcyclohexyl)ethylmalonate. Compound [S] is obtained in a higher yield if compound [Q] is brominated to yield a 2-(trans-4'-alkylcyclohexyl)-1-bromoethane and the bromoethane is substituted for a compound [R]. In toluene, compound [S] is reduced with (NaAlH$_2$(OC$_2$H$_4$OCH$_3$)$_2$ to yield compound [T], a 2-[2'-(trans-4'-alkylcyclohexyl)ethyl]propane-1,3-diol.

Compound [T] and compound [F], 3,4-difluorobenzaldehyde, are reacted and the product of the reaction is dehydrated in dichloromethane, in the presence of TsOH, used as a catalyst, to yield a 2-(3',4'-difluorophenyl)-5-[2'-(4"-alkylcyclohexyl)-ethyl]-1,3-dioxane (cis-trans mixture). The cis-trans mixture is recrystallized and the trans-trans moiety is separated out to yield compound [VI], a novel liquid crystal compound in accordance with the invention.

The trans-2-fluorophenyl-5-(trans-4'-alkylcyclohexyl-1,3-dioxane derivatives wherein A is a —CH$_2$CH$_2$— group, X is CN and Y is F can be produced by the following Reaction Scheme VI:

REACTION SCHEME VI

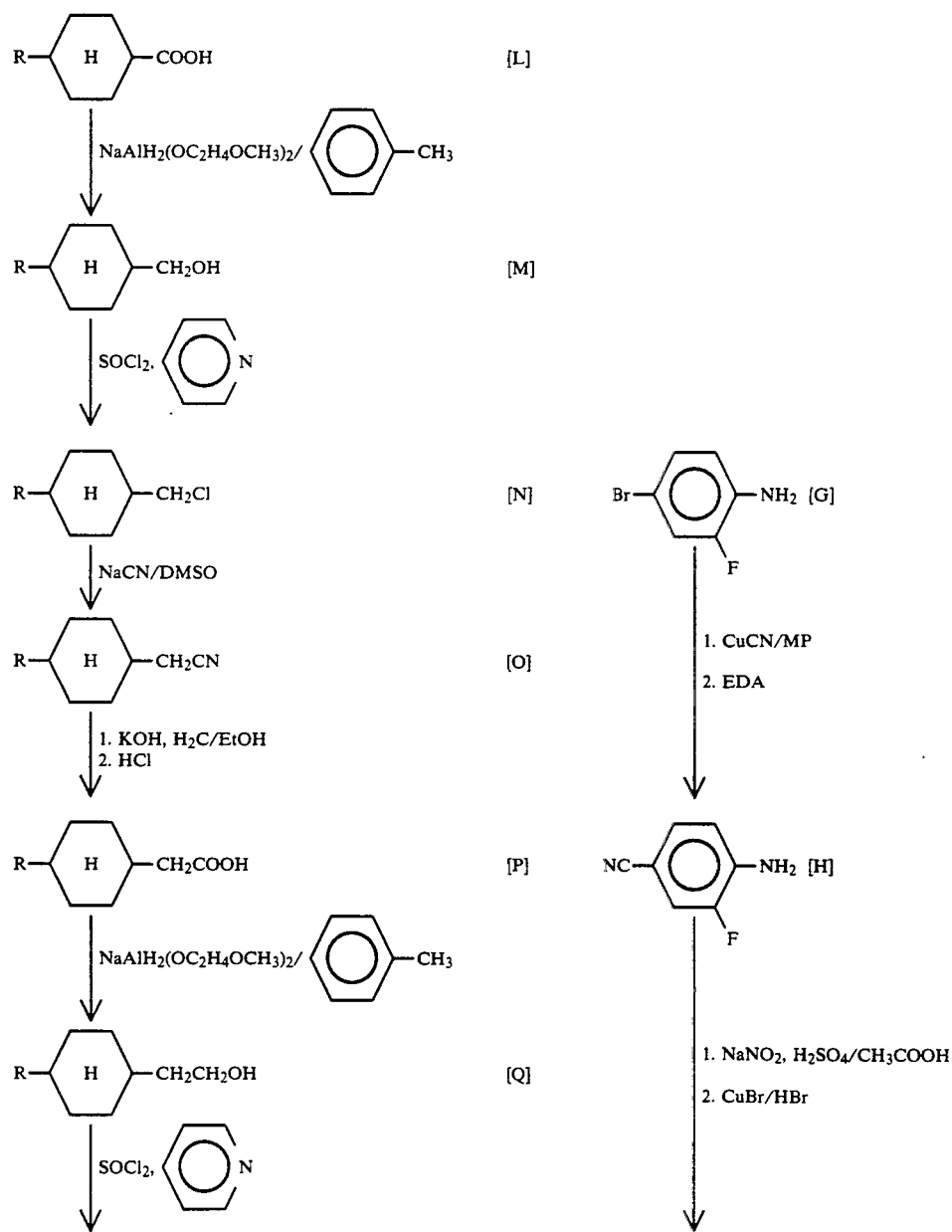

-continued
REACTION SCHEME VI

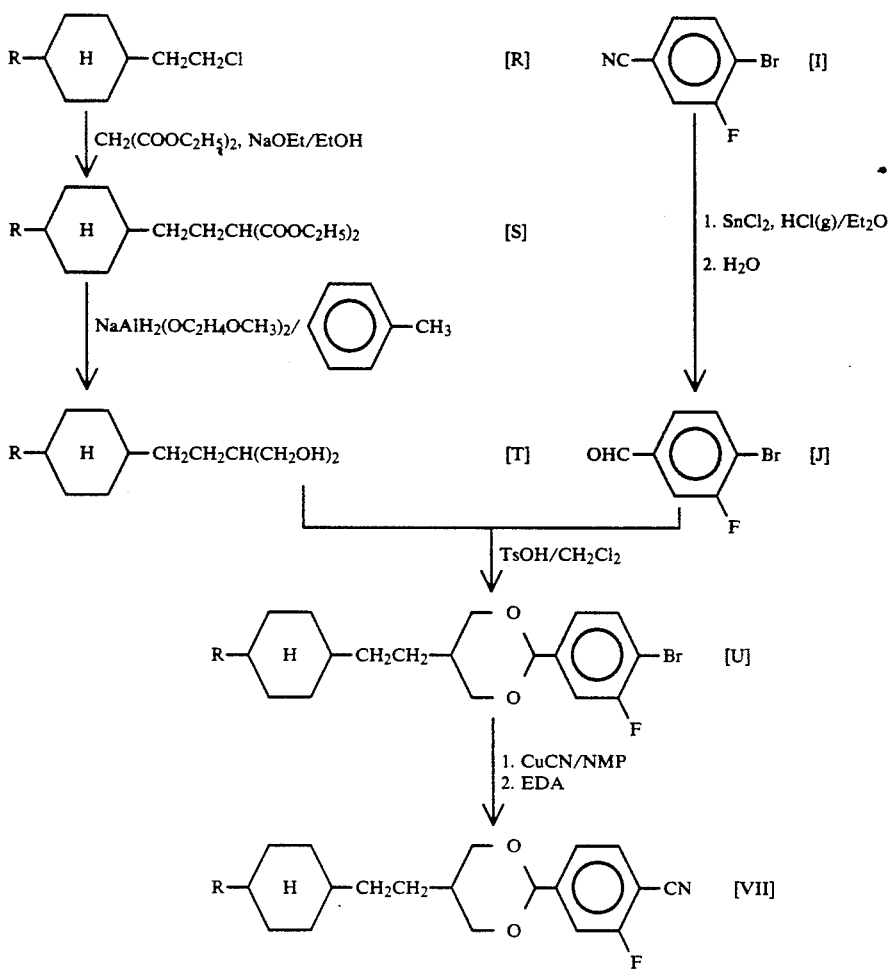

In toluene, a compound [L] a trans-4-alkylcyclohexane carboxylic acid is reduced with sodium bis(methoxyethoxy) aluminum hydride (NaAlH$_2$(OC$_2$H$_4$OCH$_3$)$_2$) to yield a compound [M], a trans-4-alkylcyclohexyl methanol. Alternatively, compound [L] is converted into a trans-4-alkylcyclohexane carbonyl chloride with thionyl chloride (SOCl$_2$) and reduced with (NaAlH$_2$(OC$_2$H$_4$OCH$_3$)$_2$ to yield compound [M].

In anhydrous pyridine, compound [M] is chlorinated with SOCl$_2$ to yield compound [N], a trans-4-alkylcyclohexyl chloromethane. In dimethyl sulfoxide (DMSO), compound [N] is cyanated with sodium cyanide (NaCN) to yield compound [O], a trans-4-alkylcyclohexyl acetonitrile.

In ethanol, compound [O] is hydrolyzed with potassium hydroxide (KOH) to form a hydrolyzate. The hydrolyzate is neutralized with HCl to yield compound [P], a trans-4-alkyl cyclohexyl acetic acid. In toluene, compound [P] is reduced with (NaAlH$_2$(OC$_2$H$_4$OCH$_3$)$_2$ to yield compound [Q], a 2-(trans-4'-alkylcyclohexyl) ethanol. Alternatively, compound P] is chlorinated to yield a trans-4-alkylcyclohexylacetyl chloride and the acetyl chloride is reduced with (NaAlH$_2$(OC$_2$H$_4$OCH$_3$)$_2$.

In anhydrous pyridine, compound [Q] is chlorinated with SOCl$_2$ to yield compound [R], a 2-(trans-4'-alkylcyclohexyl)-1-chloroethane. In anhydrous ethanol, compound [R] is alkylated with diethyl malonate and sodium ethoxide (NaOEt) to yield compound [S], a diethyl 2-(trans-4'-alkylcyclohexyl)ethylmalonate. Compound [S] is obtained in a higher yield if compound [Q] is brominated to yield a 2-(trans-4'-alkylcyclohexyl)-1-bromoethane and the bromoethane is substituted for a compound [R]. In toluene, compound [S] is reduced with (NaAlH$_2$(OC$_2$H$_4$OCH$_3$)$_2$ to yield compound [T], a 2-[2'-(trans-4'-alkylcyclohexyl)ethyl]propane-1,3-diol.

In N-methyl-2-pyrrolidinone (NMP), compound [G], a commercially available 4-bromo-2-fluoroaniline (manufactured by Aldrich) is cyanated with copper (I) cyanide to form a copper complex. The copper complex is decomposed with ethylene diamine (EDA) to yield compound [H], a 4-amino-3-fluorobenzonitrile. Alternatively, a solution of iron (III) chloride in hydrochloric acid may be used to decompose the copper complex.

In glacial acetic acid, compound [H] is diazodized with nitrocil hydrogen sulfate (HSO$_4$—ONO$_2$) prepared from sodium nitrite (NaNO$_2$) and concentrated sulfuric acid. The diazonium salt formed is brominated in hydrobromic acid with copper (I) bromide (CuBr) to yield compound [I], 4-bromo-3-fluorobenzonitrile.

In diethyl ether, compound [I] is reacted with tin (II) chloride (SnCl$_2$·) saturated with hydrogen chloride gas, to reduce the cyano group into an aldehyde group and form a tin complex. The tin complex is decomposed with hot water to yield compound [J], 4-bromo-3-fluorobenzaldehyde.

Compound [T] and compound [J] are reacted and dehydrated in dichloromethane, in the presence of TsOH, used as a catalyst, to yield a compound [U], a 2-(4'-bromo-3'-fluorophenyl)-5-[2'-(4"-alkylcyclohexyl)ethyl]-1,3-dioxane.

In NMP, compound [U] is cyanated with CuCN to form a copper complex. The copper complex is decomposed with EDA to yield a 2-(4'-cyano-3'-fluorophenyl)-5-[2'-(4"-alkylcyclohexyl)ethyl]-1,3-dioxane (cis-trans mixture). The trans-trans moiety is separated out to yield compound [VII], a novel liquid crystal compound in accordance with the invention.

A conventional 1,3-dioxane derivative having the formula

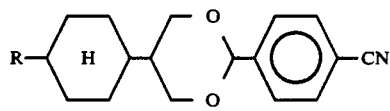

wherein R is a linear alkyl group and the cyclohexane ring and the 1,3-dioxane ring are the trans isomers, can be produced by the following Reaction Scheme VII:

REACTION SCHEME VII

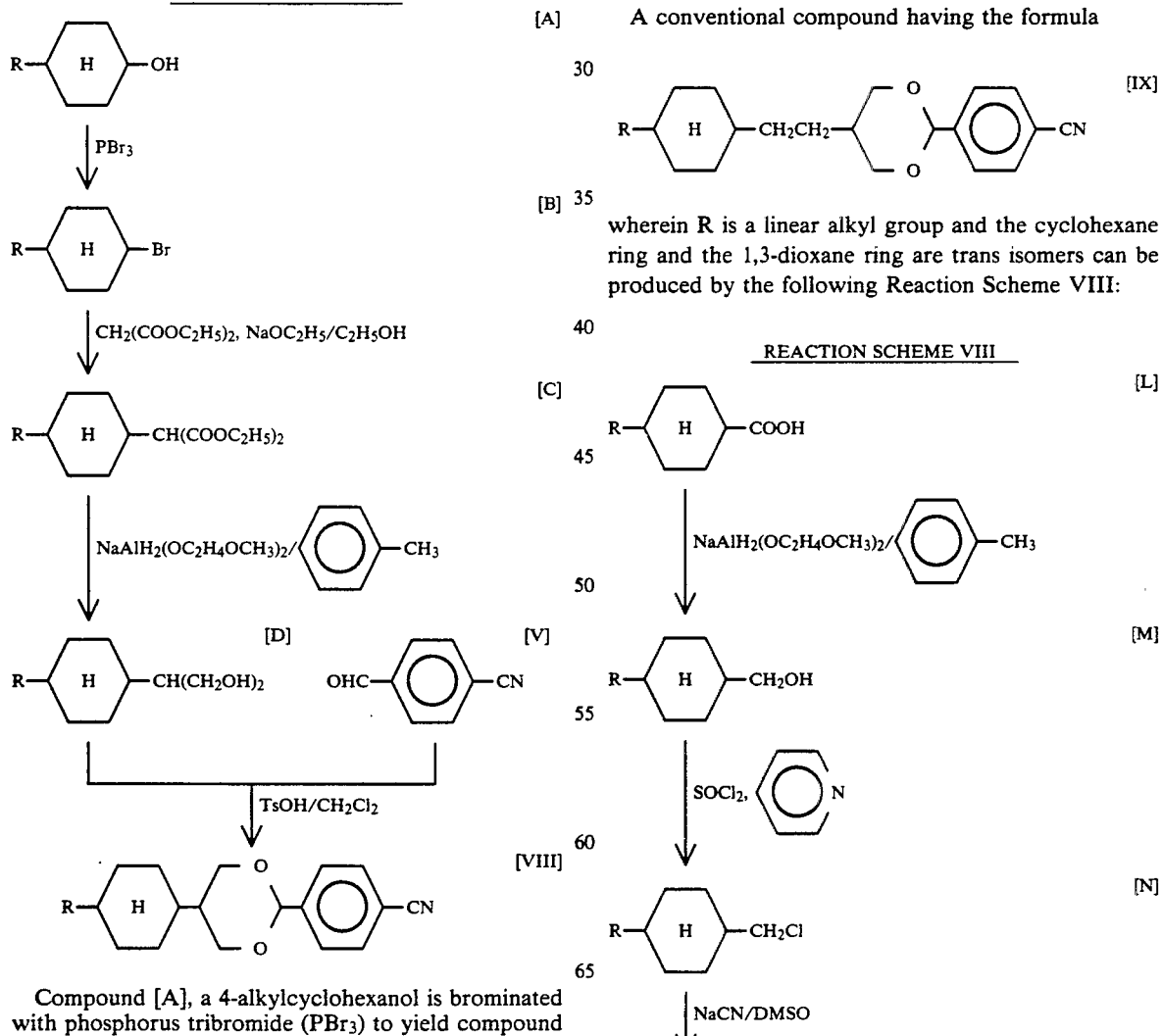

Compound [A], a 4-alkylcyclohexanol is brominated with phosphorus tribromide (PBr₃) to yield compound [B], a cis-trans mixture 4-alkyl-1-bromocyclohexane.

Compound [B] is used as a cis-trans mixture or a trans compound. If a HBr—H₂SO₄ system is used, the reaction results in a poor yield of compound [B] due to large amounts of 4-alkylcyclohexene produced as a by-product.

Compound [B] is reacted with diethyl malonate in anhydrous ethanol in the presence of sodium ethoxide (NaOC₂H₅) to yield compound [C], a diethyl-4-alkylcyclohexyl malonate. The yield of compound [C] is low due to the formation of 4-alkylcyclohexene, a by-product of the reaction.

Compound [C] is reduced with sodium bis(methoxyethoxy) aluminum hydride (NaAlH₂(OC₂H₄OCH₃)₂) in toluene to yield compound [D], a 2-(4,-alkylcyclohexyl) propane-1,3-diol (cis-trans mixture.

In dichloromethane, in the presence of TsOH, used as a catalyst, compound [D] and compound [V], 4-cyanobenzaldehyde are reacted to yield a 2-(4'-cyanophenyl)-5-(4'-alkylcyclohexyl)-1,3-dioxane. The cyclohexane ring and the 1,3-dioxane ring are both cis-trans mixtures. The cis-trans mixture is recrystallized and the trans-trans moiety is separated out to yield conventional compound [VIII].

A conventional compound having the formula

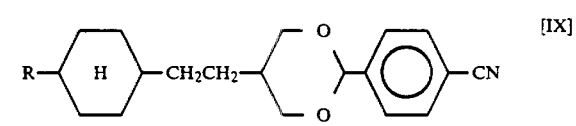

wherein R is a linear alkyl group and the cyclohexane ring and the 1,3-dioxane ring are trans isomers can be produced by the following Reaction Scheme VIII:

REACTION SCHEME VIII

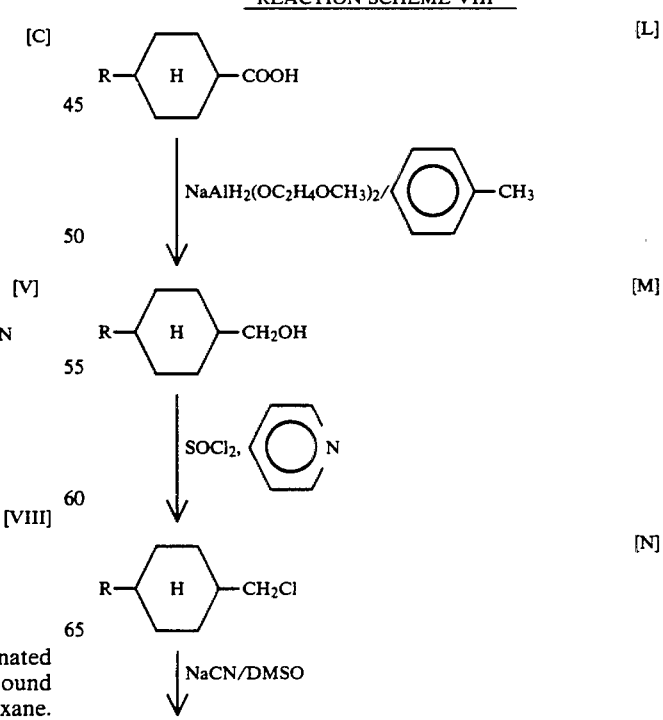

-continued
REACTION SCHEME VIII

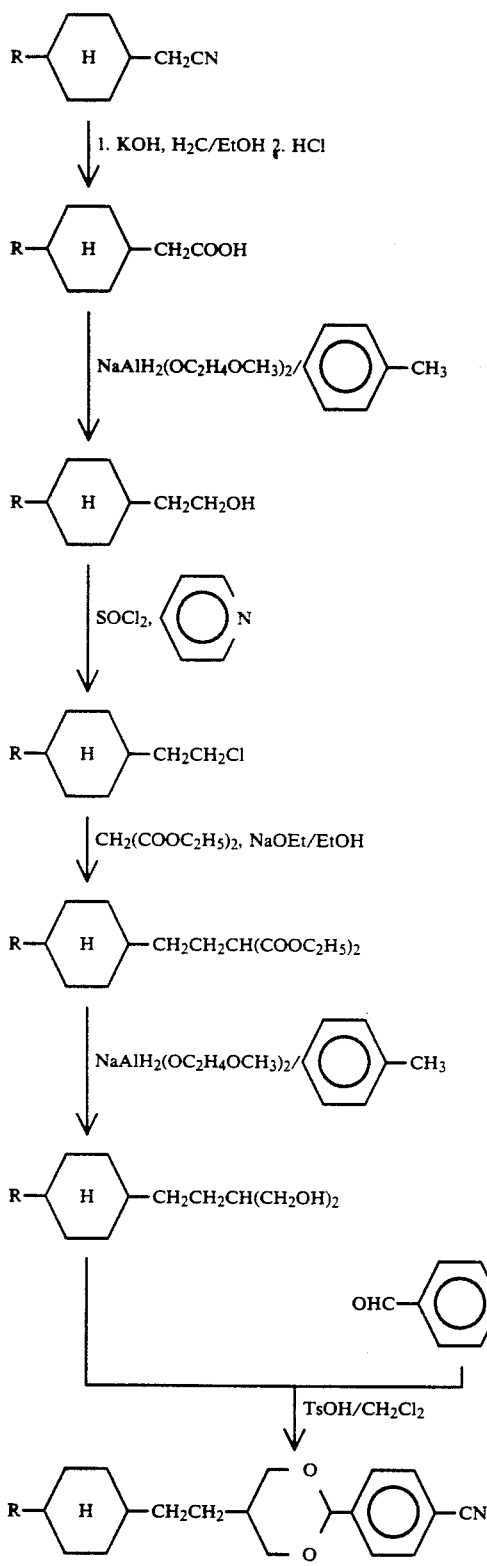

In toluene, a compound [L] a trans-4-alkylcyclohexane carboxylic acid is reduced with sodium bis(methoxyethoxy) aluminum hydride (NaAlH$_2$(OC$_2$H$_4$OCH$_3$)$_2$) to yield a compound [M], a trans-4-alkylcyclohexyl methanol. Alternatively, compound [L] is converted into a trans-4-alkylcyclohexane carbonyl chloride with thionyl chloride (SOCl$_2$) and reduced with (NaAlH$_2$(OC$_2$H$_4$OCH$_3$)$_2$ to yield compound [M].

In anhydrous pyridine, compound [M] is chlorinated with SOCl$_2$ to yield compound [N], a trans-4-alkylcyclohexyl chloromethane. In dimethyl sulfoxide (DMSO), compound [N] is cyanated with sodium cyanide (NaCN) to yield compound [O], a trans-4-alkylcyclohexyl acetonitrile.

In ethanol, compound [O] is hydrolyzed with potassium hydroxide (KOH) to form a hydrolyzate. The hydrolyzate is neutralized with HCl to yield compound [P], a trans-4-alkyl cyclohexyl acetic acid. In toluene, compound [P] is reduced with (NaAlH$_2$(OC$_2$H$_4$OCH$_3$)$_2$ to yield compound [Q], a 2-trans-4'-alkylcyclohexyl) ethanol. Alternatively, compound [P] is chlorinated to yield a trans-4-alkylcyclohexylacetyl chloride and the acetyl chloride is reduced with (NaAlH$_2$(OC$_2$H$_4$OCH$_3$)$_2$.

In anhydrous pyridine, compound [Q] is chlorinated with SOCl$_2$ to yield compound [R], a 2-(trans-4'-alkylcyclohexyl)-1-chloroethane. In anhydrous ethanol, compound [R] is alkylated with diethyl malonate and sodium ethoxide (NaOEt) to yield compound [S], a diethyl 2-(trans-4'-alkylcyclohexyl)ethylmalonate. Compound [S] is obtained in a higher yield if compound [Q] is brominated to yield a 2-(trans-4'-alkylcyclohexyl)-1-bromoethane and the bromoethane is substituted for a compound [R]. In toluene, compound [S] is reduced with (NaAlH$_2$(OC$_2$H$_4$OCH$_3$)$_2$ to yield compound [T], a 2-[2'-(trans-4'-alkylcyclohexyl)ethyl]propane-1,3-diol.

In dichloromethane, in the present of TsOH, acting as a catalyst, compound [T] is reacted with compound [V], a commercially available 4-cyanobenzaldahyde, to yield a 2-(4'-cyanophenyl)-5-[2'-(4''-alkylcyclohexyl) ethyl]-1,3-dioxane. The cyclohexane ring and the 1,3-dioxane ring are both cis-trans mixtures. The cis-trans mixture is recrystallized and the trans-trans moiety is separated out to yield conventional compound [IX], a trans-2-(4'-cyanophenyl)-5-[2'-(trans-4''-butylcyclohexyl) ethyl]-1,3-dioxane.

The following examples are set forth by way of illustration to show preparation of the trans-2-fluorophenyl-5-(trans-4'-alkylcyclohexyl)-1,3-dioxane derivatives in accordance with the invention. They are set forth for purposes of illustration only, and are not intended in a limiting sense.

EXAMPLE 1

Preparation of trans-2-(4'-fluorophenyl)-5-(trans-4'-propylcyclohexyl)-1,3- dioxane:

Step 1

142 g (1.0 mol) of trans-4-propylcyclohexanol was stirred at room temperature and 136 g (0.5 mol) of PBr$_3$ was added drop-wise. The reaction was exothermic and reached about 80° C. The product of the reaction was stirred over a hot water bath at 70° C. for 1 hour, cooled to room temperature, and poured into ice water to decompose the excess PBr$_3$. The oily layer was separated out and the aqueous layer was extracted with chloroform. The oily layers were combined and washed with water. The chloroform was distilled off the washed mixture. The oily residue was distilled in a vacuum (b.p. 97° C./14 mmHg) to yield 180 g (0.88 mol) of 4-propyl-1-bromocyclohexane.

Step 2

In a solution of 31 g (1.35 mol) of sodium in 660 cm³ of anhydrous ethanol, 216 g (1.35 mol) of diethyl malonate and 180 g (0.88 mol) of 4-propyl-1-bromocyclohexane were sequentially dissolved. The resulting solution was refluxed for 10 hours over a hot water bath. The product of the reaction was cooled to room temperature. The NaBr crystals formed were separated out by filtration and the ethanol was distilled off the filtrate. The residue was combined with water to separate out the oily layer. The aqueous layer was extracted with chloroform, combined with the oily layer, and washed with water. The chloroform was distilled off and the oily residue was distilled under a vacuum (b.p. 138° C./1.4 mmHg) to yield 108 g (0.38 mol) of diethyl-4-propylcyclohexyl malonate. As an initial fraction, about 50 g of 4-propylcyclohexene was obtained.

Step 3

340 cm³ (1.2 mol) of 70% (NaAlH₂(OC₂H₄OCH₃)₂ solution in toluene was dissolved in 340 cm³ of anhydrous toluene solution and stirred at room temperature. While stirring, 57 g (0.2 mol) of diethyl 4-propylcyclohexyl malonate was added drop-wise over 30 minutes. The resulting solution was stirred over a hot water bath at 80° to 90° C. for 5 hours and cooled at room temperature. While stirring continuously, 50 cm³ of water and 100 cm³ of an aqueous 15% hydrochloric acid solution were sequentially added drop-wise to the cooled solution. The oily layer was separated out and the aqueous layer was extracted with toluene. The two layers were combined and washed with an aqueous 10% hydrochloric acid solution and water and the toluene was distilled off. The residue was recrystallized from hexane to yield 18 g (0.09 mol) of 2-(4'-propylcyclohexyl) propane-1,3-diol.

Step 4

In 40 cm³ of dichloromethane, 1.5 g (0.008 mol) of 2-(4'-propylcyclohexyl) propane-1,3-diol, 1.4 g (0.01 mol) of 4-fluorobenzaldehyde (manufactured by Aldrich), and 0.1 g of TsOH were refluxed for 3 hours over a hot water bath fitted with a Dean-Stark trap and the water formed was continuously removed from the reaction system. The reaction solution was washed with water and the dichloromethane was distilled off. The distillation residue was recrystallized from a solvent mixture of acetone and methanol to yield 1.1 g (0.004 mol) of trans-2-(4'-fluorophenyl)-5-(trans-4'-propylcyclohexyl)-1,3-dioxane. The phase transition points of this compound, measured by DSC, were:

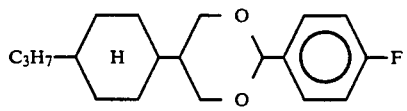

wherein C is the crystal phase, N is the nematic phase and I is the isotropic liquid phase.

The following are other examples of the compounds in accordance with the invention prepared following the procedures of Example 1:

Trans-2-(4'-fluorophenyl)-5-(trans-4'-methylcyclohexyl)-1,3-dioxane

Trans-2-(4'-fluorophenyl)-5-(trans-4'-ethylcyclohexyl)-1,3-dioxane

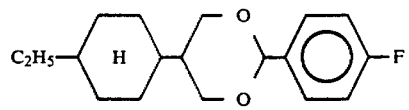

Trans-2-(4'-fluorophenyl)-5-(trans-4'-butylcyclohexyl)-1,3-dioxane

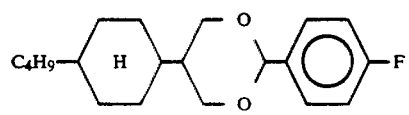

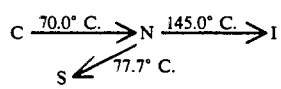

Trans-2-(4'-fluorophenyl)-5-(trans-4'-pentylcyclohexyl)-1,3-dioxane

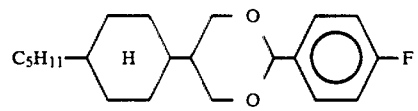

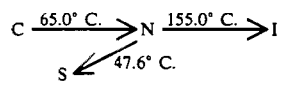
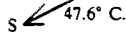

Trans-2-(4'-fluorophenyl)-5-(trans-4'-hexylcyclohexyl)-1,3-dioxane

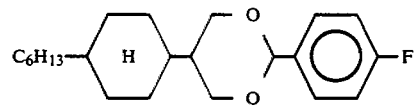

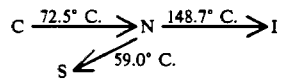
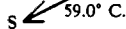

Trans-2-(4'-fluorophenyl)-5-(trans-4'-heptlcyclohexyl)-3-dioxane

Trans-2-(4'-fluorophenyl)-5-(trans-4'-octylcyclohexyl)-1,3-dioxane

Trans-2-(4'-fluorophenyl)-5-(trans-4'-nonylcyclohexyl)-1,3-dioxane

Trans-2-(4'-fluorophenyl)-5-(trans-4'-decylcyclohexyl)-1,3-dioxane

EXAMPLE 2

Preparation of trans-2-(3',4'-diflurophenyl)-5-(trans-4'-propylcyclohexyl)-1,3-dioxane Step 1 to Step 3

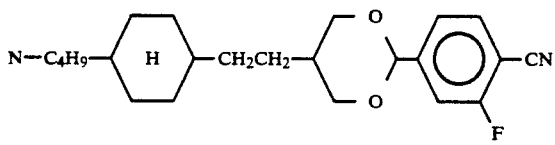

2-(4'-propylcyclohexyl)propane-1,3-diol was prepared in the same manner as in Steps 1 through 3 of Example 1.

Step 4

In 40 cm$^3$ of dichloromethane, 1.5 g (0.008 mol) of 2-(4'-propylcyclohexyl)propane-1,3-diol, 1.5 g (0.01 mol) of 3,4-difluorobenzaldehyde (manufactured by Aldrich), and 0.1 g of TsOH were refluxed for 3 hours over a hot water bath fitted with a Dean-Stark trap and the water formed was removed continuously from the reaction system. The reaction solution was washed with water and the dichloromethane was distilled off. The distillation residue was recrystallized from a solvent mixture of acetone and methanol to yield 1.6 g (0.005 mol) of trans-2-(3',4'-difluorophenyl)-5-(trans-4'-propylcyclohexyl)-1,3-dioxane. The phase transition points, measured by DSC, were:

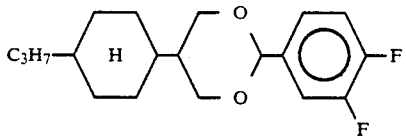

$C \xrightarrow{88.5° C.} N \xrightarrow{105.1° C.} I$ wherein C is the crystal phase, N is the nematic phase and I is the isotropic liquid phase.

The following are other examples of the compounds in accordance with the invention prepared following the procedures of Example 2:

Trans-2-(4'-difluorophenyl)-5-(trans-4'-methylcyclohexyl)-1,3-dioxane

Trans-2-(4'-difluorophenyl)-5-(trans-4'-ethylcyclohexyl)-1,3-dioxane

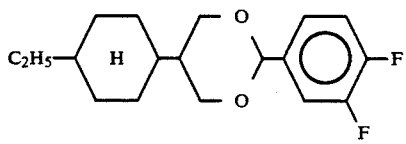

$C \xrightarrow{86.2° C.} I$

Trans-2-(3',4'-difluorophenyl)-5-(trans-4'-butylcyclohexyl)-1,3-dioxane

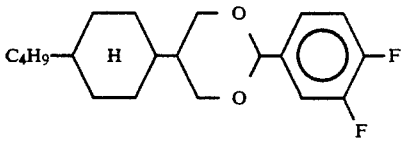

$C \xrightarrow{89.8° C.} N \xrightarrow{109.7° C.} I$

Trans-2-(3',4'-difluorophenyl)-5-(trans-4'-pentylcyclohexyl)-1,3-dioxane

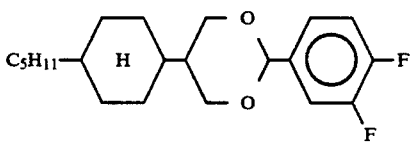

$C \xrightarrow{77.0° C.} N \xrightarrow{113.8° C.} I$

Trans-2-(3',4'-difluorophenyl)-5-(trans-4'-hexylcyclohexyl)-1,3-dioxane

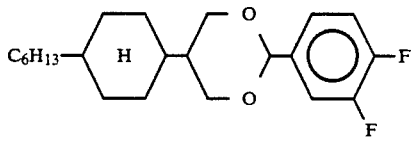

$C \xrightarrow{70.1° C.} N \xrightarrow{115.0° C.} I$

Trans-2-(3',4'-difluorophenyl)-5-(trans-4'-heptylcyclohexyl)-1,3-dioxane

Trans-2-(3',4'-difluorophenyl)-5-(trans-4'-octylcyclohexyl)-1,3-dioxane

Trans-2-(3',4'-difluorophenyl)-5-(trans-4'-nonylcyclohexyl)-1,3-dioxane

Trans-2-(3',4'-difluorophenyl)-5-(trans-4'-decylcyclohexyl)-1,3-dioxane

EXAMPLE 3

Preparation of trans-2-(4'-cyano-3'-fluorophenyl)-5-(trans-4'-propylcyclohexyl)-1,3-dioxane:

Step 1 to Step 3

2-(4'-propylcyclohexyl)propane-1,3-diol was prepared in the same manner as in Steps 1 through 3 of Example 1.

Step 4

50 g (0.26 mol) of 4-bromo-2-fluoroaniline and 30 g (0.34 mol) of CuCN were dissolved in 130 cm$^3$ of NMP and the solution was refluxed with a mantle heater for 2 hours. The reaction solution was cooled to room temperature. 42 cm$^3$ of EDA was added to the cooled solution and the solution was poured into 300 cm$^3$ of ice water. The resulting mixture was extracted with chloroform and washed with an aqueous EDA solution and water. The chloroform was distilled off the washed mixture. The distillation residue was dissolved in ether and washed with water to remove the NMP. The residue was distilled in a vacuum (b.p. 165° C./23 mmHg) to yield 28 g (0.21 mol) of 4-amino-3-fluorobenzonitrile.

It was necessary to perform the distillation under an elevated degree of vacuum since the product was extremely sublimable and the crystals adhered to the output of the distillation tube and clogged the tube.

Step 5

120 cm³ of concentrated sulfuric acid was stirred over an ice water bath and 15 g (0.22 mol) of pulverized NaNO₂ was added at a rate slow enough to keep the temperature below 30° C. The resulting mixture was stirred over a hot water bath at 50° C. until the NaNO₂ crystals were thoroughly dissolved. The solution was stirred over an ice water bath and 200 cm³ of glacial acetic acid was added drop-wise over 30 minutes. While stirring, 28 g (0.21 mol) of 4-amino-3-fluorobenzonitrile was added to the solution at a rate slow enough to keep the temperature in the range between 20° and 25° C. At this temperature, the resulting mixture was stirred until the crystals were thoroughly dissolved to form a diazonium salt solution. A solution of 44 g (0.3 mol) of CuBr in 120 cm³ of an aqueous 47% hydrobromic acid solution was stirred vigorously over an ice water bath and the diazonium salt solution was added drop-wise over one hour. After the drop-wise addition was completed, the resulting mixture was stirred over an ice water bath for 2 hours and allowed to stand overnight. The crystals formed were filtered out and washed with glacial acetic acid. The crystals were fluorobenzonitrile.

Step 6

A mixture of 59 g (0.31 mol) of anhydrous SnCl₂ and 320 cm³ of diethyl ether was placed on an ice water bath and saturated with hydrogen chloride gas generated by the drop-wise addition of concentrated sulfuric acid to concentrated hydrochloric acid until the SnCl₂ assumed a liquid state and the mixture was dried with concentrated sulfuric acid. 31 g (0.16 mol) of 4-bromo-3-fluorobenzonitrile was added to the mixture and the resulting mixture was stirred at room temperature for 1 hour and allowed to stand overnight. 300 cm³ of water was added to the reaction product and the mixture was stirred over a hot water bath at 50° C. The diethyl ether was distilled off. The oily layer was separated out and the aqueous layer was extracted with ether. The two layers were combined, washed with water, and dried overnight with anhydrous Na₂SO₄. Diethyl ether was distilled off the resulting dried mixture. Diethyl ether was distilled off the distillation residue. The distillation residue was distilled under a vacuum (b.p. 122° C./25 mmHg) to yield 26 g (0.13 mol) of 4-bromo-3-fluorobenzaldehyde.

Step 7

A solution of 4.0 g (0.02 mol) of 2-(4'-propylcyclohexyl)propane-1,3-diol, 5.1 g (0.025 mol) of 4-bromo-3-fluorobenzaldehyde, and 0.2 g of TsOH in 100 cm³ of dichloromethane was refluxed over a hot water bath fitted with a Dean-Stark trap for 3 hours and the water formed was continuously removed from the reaction system. The resulting solution was washed with water and dichloromethane was distilled off. The residue was recrystallized from acetone to yield 6.2 g (0.016 mol) of 2-(4'-bromo-3'-fluorophenyl)-5-(trans-4'-propylcyclohexyl)-1,3-dioxane. This compound contained about 10% of the cis isomer of the 1,3-dioxane ring.

Step 8

In 40 cm³ of NMP, 6.2 g (0.016 mol) of 2-(4'-bromo-3'-fluorophenyl)-5-(trans-4'-propylcyclohexyl)-1,3-dioxane and 2.2 g (0.024 mol) of CuCN were refluxed with a mantle heater for 2 hours.

The reaction product was cooled to room temperature. 2.5 cm³ of EDA was added to the cooled reaction product and the solution was poured into 60 cm³ of ice water. The resulting mixture was extracted with chloroform, washed sequentially with an aqueous solution of EDA and water, and the chloroform was distilled off. The residue was disolved in hexane, washed with water to separate out the NMP, and the hexane was distilled off. The residue was recrystallized once from a solvent mixture of acetone and methanol, and treated through a silica gel column with chloroform as the solvent. The chloroform was distilled off and the residue was repeatedly recrystallized from a solvent mixture of acetone and methanol until there was no cis isomer left to yield 1.8 g 0.005 mol) of trans-2-(4,-cyano-3'-fluorophenyl)-5-(trans-4'-propylcyclohexyl)-1,3-dioxane. The decomposition of raw materials and the transition from the trans isomer to the cis isomer occurred as secondary rections while refluxing. The phase transition points of this compound, measured by DSC, were:

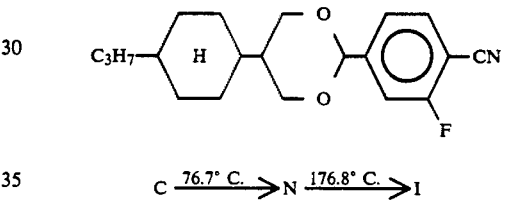

$$C \xrightarrow{76.7° \text{ C.}} N \xrightarrow{176.8° \text{ C.}} I$$

wherein C is the crystal phase, N is the nematic phase, and I is the isotropic liquid phase.

The following are other examples of the compounds in accordance with the invention prepared following the procedures of Example 3:

Trans 2-(4'-cyano-3 -fluorophenyl)-5-(trans-4'-methylcyclohexyl)-1,3-dioxane.

Trans-2-(4'-cyano-3'-fluorophenyl)-5-(trans-4'-ethylcyclohexyl)-1,3-dioxane.

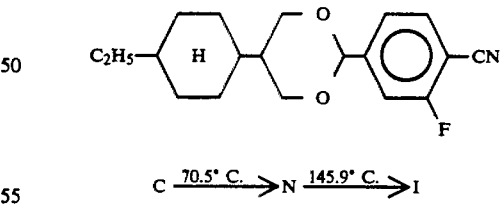

$$C \xrightarrow{70.5° \text{ C.}} N \xrightarrow{145.9° \text{ C.}} I$$

Trans-2-(4'-cyano-3'-fluorophenyl) -5-(trans-4'-butylcyclohexyl)-1,3-dioxane.

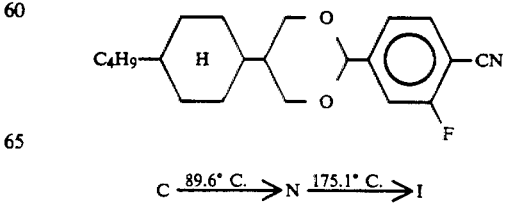

$$C \xrightarrow{89.6° \text{ C.}} N \xrightarrow{175.1° \text{ C.}} I$$

Trans-2-(4'-cyano-3'-fluorophenyl)-5-(trans-4'-pentyl-cyclohexyl)-1,3-dioxane.

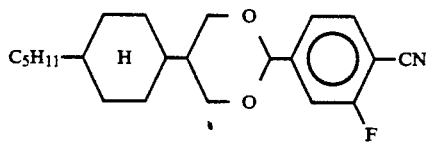

Trans-2-(4'-cyano-3'-fluorophenyl)-5-(trans-4'-hexylcyclohexyl)-1,3-dioxane.

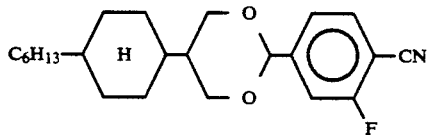

Trans-2-(4'-cyano-3'-fluorophenyl)-5-(trans-4'-heptylcyclohexyl)-1,3-dioxane.
Trans-2-(4'-cyano-3'-fluorophenyl)-5-(trans-4'-octylcyclohexyl)-1,3-dioxane.
Trans-2-(4'-cyano-3'-fluorophenyl)-5-(trans-4'-nonylcyclohexyl)-1,3-dioxane.
Trans-2-(4'-cyano-3'-fluorophenyl)-5-(trans-4'-decylcyclohexyl)-1,3-dioxane.

EXAMPLE 4

Preparation of trans-2-(4'-fluorophenyl)-5-[2'-(trans-4"-butylcyclohexyl)ethyl]-1,3-dioxane:

Step 1

55 g (0.30 mol) of trans-4-butylcyclohexane carboxylic acid was dispersed in 200 c; of toluene and stirred. 250 cm³ (0.90 mol) of a 70% NaAlH$_2$(OC$_2$H$_4$OCH$_3$)$_2$ solution was added drop-wise to the solution at a rate to gently reflux the toluene. After the drop-wise addition was completed, the resulting mixture was stirred over a hot water bath at 90° C. for 3 hours. The solution was cooled to room temperature and, while stirring, 10 cm³ of water and 300 cm³ an aqueous 15% hydrochloric acid solution were added drop-wise while stirring. The oily layer was separated out and the aqueous layer was extracted with toluene. The two layers were combined and washed with an aqueous 15% hydrochloric acid solution and water. The toluene was distilled off the washed mixture. The oily residue was distilled in a vacuum (b.p. 100° C./2 mmHg) to yield 37 g (0.11 mol) of trans-4-butylcyclohexyl methanol.

Alternatively, trans-4-butylcyclohexyl menthanol was prepared by chlorinating trans-4-butylcyclohexane carboxylic acid and reducing trans-4-butylcyclohexane carbonyl chloride with NaAlH$_2$(OC$_2$H$_4$OCH$_3$)$_2$ as follows: 55 g (0.30 mol) of trans-4-butylcyclohexane carboxylic acid and 53 g (0.45 mol) of SOCl$_2$ were refluxed on a hot water bath and the excess SOCl$_2$ was distilled off in a vacuum to form an oily residue. 110 cm³ (0.39 mol) 70% NaAlH$_2$(OC$_2$H$_4$OCH$_3$)$_2$ solution in toluene was dissolved in 110 cm³ of anhydrous toluene and stirred and the oily residue was added drop-wise to the solution at a rate to gently reflux the toluene. After the drop-wise addition was completed, the resulting mixture was stirred over a hot water bath at 90° C. for 3 hours. The solution was cooled to room temperature and while stirring, 10 cm³ of water and 300 cm³ of an aqueous 15% hydrochloric acid solution were added drop-wise. The oily layer was separated out and the aqueous layer was extracted with toluene. The two layers were combined and washed with an aqueous 15% hydrochloric acid solution and water. The toluene was distilled off the washed mixture. The oily residue was distilled in a vacuum (b.p. 100° C./2 mmHg) to yield 44 g (0.26 mol) of trans-4-butylcyclohexyl methanol.

Although the second method of forming trans-4-butylcyclohexyl methanol requires an extra step in the reaction (chlorinating trans-4-butylcyclohexyl methanol), the second method consumes less of the reducing agent and results in a higher yield of trans-4-butylcyclohexyl methanol.

Step 2

Over an ice water bath, 37 g (0.22 mol) of trans-4-butylcyclohexyl methanol and 18 g (0.23 mol) of anhydrous pyridine were stirred and 32 g (0.27 mol) of SOCl$_2$ was added drop-wise to the mixture. The resulting reaction product was stirred on a mantle heater at a temperature of between about 105 and 110° C. for 3 hours. The reaction product was cooled to room temperature and poured into a breaker containing concentrated hydrochloric acid and ice. The oily layer was separated out and the aqueous layer was extracted with chloroform. The two layers were combined and washed with an aqueous 10% hydrochloric acid solution and water. The chloroform was distilled off. The oily residue was distilled in a vacuum (b.p. 80° C./3 mmHg) to yield 38 g (0.20 mol) of trans-4-butylcyclohexyl chloromethane.

Step 3

In 40 cm³ of DMSO, 38 g (0.20 mol) of trans-4-butyl cyclohexylchloromethane and 12 g (0.24 mol) of NaCN were stirred and heated with a mantle heater to 140° C. The reaction product was cooled to room temperature, combined with 100 cm³ of water, extracted with chloroform, and washed with water. The chloroform was distilled off. The oily residue was subjected to vacuum distillation (b.p. 90° C./3 mmHg) to yield 34 g (0.19 mol) of trans-4-butylcyclohexyl acetonitrile.

Step 4

A solution of 34 g (0.19 mol) of trans-4-butylcyclohexyl acetonitrile, 43 g (0.76 mol) of KOH, and 34 cm³ of water in 190 cm³ of ethanol was refluxed over a hot water bath until the generation of ammonia gas ceased (about 10 hours). Ammonia gas was detected using phenolphthalein test paper. The reaction solution was cooled to room temperature and ethanol was distilled off. The residue was dissolved in 100 cm³ of water. The resulting solution was poured into a beaker containing 100 g of water and 100 cm³ of concentrated hydrochloric acid. The crystals precipitated in the beaker were separated out by filtration and washed with water. The crystals were recrystallized from a solvent mixture of methanol and water to yield 37 g (0.19 mol) of trans-4-butylcyclohexyl acetic acid.

Step 5

37 g (0.19 mol) of trans-4-butylcyclohexyl acetic acid was dispersed in 190 cm³ of anhydrous toluene and stirred and 160 cm³ (0.57 mol) of a 70% NaAlH$_2$(OC$_2$H$_4$OCH$_3$)$_2$ solution in toluene was added drop-wise at a rate to gently flux the toluene. After the drop-wise addition was completed, the resulting mixture was stirred and 40 cm³ of water and 500 cm³ of an aqueous 15% hydrochloric acid solution were added drop-wise. The oily layer was separated out and the aqueous layer was extracted with toluene. The two layers were combined, washed with an aqueous 10% hydrochloric acid solution and water and the toluene was distilled off. The oily residue was subjected to vacuum distillation (b.p. 103° C./3 mmHg) to yield 31 g (0.17 mol) of 2-trans-4'-butylcyclohexyl-ethanol. Alternatively, 2-trans-4'-butylcyclohexyl-ethanol was obtained in a high yield by chlorinating trans-4'-butylcyclohexyl acetic acid with SOCl$_2$ to prepare trans-4'-butylcyclohexyl chloride which was reduced with NaAlH$_2$(OC$_2$H$_4$OCH$_3$)$_2$.

Step 6

A mixture of 31 g (0.17 mol) of 2-(trans-4'-butylcyclohexyl) ethanol and 14 g (0.18 mol) of anhydrous pyridine was stirred over an ice water bath and 25 g (0.21 mol) of SOCl$_2$ was added drop-wise to the mixture. The resulting reaction product was stirred and heated with a mantle heater at 105° to 110° C. for 3 hours. The reaction product was cooled to room temperature and poured into a beaker containing ice and concentrated hydrochloric acid. The oily layer was separated out and the aqueous layer was extracted with chloroform. The two layer were combined and washed with an aqueous 10% hydrochloric acid solution and water. The chloroform was distilled off. The residual liquid was distilled in a vacuum (b.p. 96° C./3 mmHg) to yield 30 g (0.15 mol) of 2-(trans-4'-butylcyclohexyl)-1-chloroethane.

Step 7

A solution of 3 5 g (0.15 mol) of sodium in 150 cm³ of anhydrous ethanol, 29 g (0.18 mol) of diethyl malonate and 30 g (0.15 mol) of 2-(trans-4-butylcyclohexyl)-1-chloroethane was refluxed over a hot water bath for 10 hours. The solution was cooled to room temperature. The NaCl formed was separated out by filtration and the filtrate was distilled to remove ethanol. The residue was combined with water, extracted with chloroform, and sequentially washed with water, an aqueous 10% hydrochloric acid solution, and water. The chloroform was distilled off. The residual liquid was subjected to vacuum distillation (b.p. 165° C./3 mmHg) to yield 29 g (0.08 mol) of diethyl 2-(butylcyclohexyl)ethyl malonate. The yield was 76% when the procedure was repeated and 2-(trans-4,-butylcyclohexyl)-1-bromoethane was used in place of 2-(trans-4'-butylcyclohexyl)-1-chloroethane.

Step 8

130 cm³ (0.48 mol) of a 70% NaAlH$_2$(OC$_2$H$_4$OCH$_3$)$_2$ solution in toluene was dissolved in 130 cm³ of anhydrous toluene and stirred. 29 g (0.08 mol) of diethyl 2-(trans-4'-butylcyclohexyl) ethyl malonate was added drop-wise to the solution. After the drop-wise addition was completed, the resulting mixture was heated over a hot water bath at 80° to 90° C. for 5 hours. The reaction product was cooled to room temperature and 30 cm³ of water and 400 cm³ of an aqueous 15% hydrochloric acid solution were added drop-wise while continuously stirring. The oily layer was separated out and the aqueous layer was extracted with toluene. The two layers were combined and washed with an aqueous 10% hydrochloric acid solution and water. The toluene was distilled off. The residue was recrystallized from hexane to yield 14 g (0.06 mol) of 2-[2'-(trans-4"-butylcyclohexyl)ethyl]propane-1,3,diol.

Step 9

A solution of 2.4 g (0.01 mol) of 2-[2'-(trans-4"-butylcyclohexyl)ethyl]propane-1,3-diol, 1.8 g (0.01 mol) of 4-fluorobenzaldehyde (manufactured by Aldrich) and 0.1 g of TsOH in 50 cm³ of dichloromethane was refluxed for 3 hours over a hot water bath with a Dean-Stark trap. The resulting solution was washed with water and the dichloromethane was distilled off. The residue was recrystallized from a solvent mixture of acetone and methanol to yield 3.0 g (0.008 mol) of trans-2-(4'-fluorophenyl)-5-[2'-(trans-4"-butylcyclohexyl)ethyl]-1,3-dioxane. The phase transition temperature of this compound, measured by DSC, was:

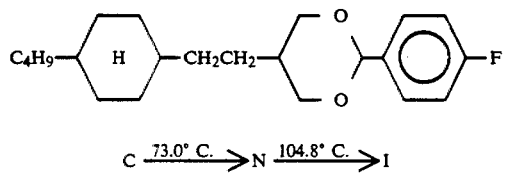

wherein C is the crystal phase, N is the nematic phase, and I is the isotropic liquid phase.

The following are other examples of the compounds in accordance with the invention prepared following the procedures of Example 4:

Trans-2-(4'-fluorophenyl)-5-[2 - (trans-4"-methylcyclohexyl)-ethyl]-1,3-dioxane

Trans-2-(4'-fluorophenyl)-5-[2'-(trans-4"-ethylcyclohexyl)ethyl]-1,3-dioxane

Trans-2-(4'-fluorophenyl)- 5-[2'-(trans-4"-propylcyclohexyl)ethyl]-1,3-dioxane

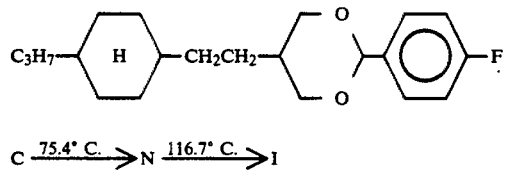

Trans-2-(4 -fluorophenyl)-5-[2 -(trans-4"-pentylcyclohexyl)-ethyl]-1,3-dioxane

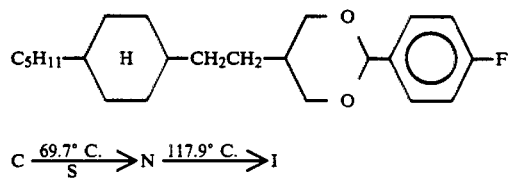

Trans-2-(4'-fluorophenyl)-5-[2 -(trans-4"-hexylcyclohexyl)-ethyl]-1,3-dioxane

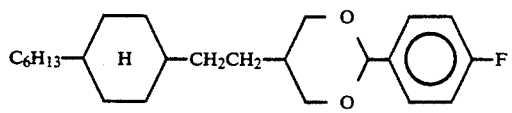

$$C \xrightarrow{77.4°\ C.} N \xrightarrow{113.5°\ C.} I$$

Trans-2-(4'-fluorophenyl)-5-[2'-(trans-4''-heptylcyclohexyl)-ethyl]-1,3-dioxane

Trans-2-(4'-fluorophenyl)-5-[2'-(trans-4''-octylcyclohexyl)-ethyl]-1,3-dioxane

Trans-2-(4'-fluorophenyl)-5-[2'-(trans-4''-nonylcyclohexyl)-ethyl]-1,3-dioxane

Trans-2-(4'-fluorophenyl)-5-2 trans-4''-decylcyclohexyl)-ethyl]-1,3-dioxane

EXAMPLE 5

Preparation of trans-2-(3',4'-difluorophenyl)-5-[2'-(trans-4''-butylcyclohexyl)-ethyl]-1,3-dioxane

Step 1 to Step 8

2-[2'-(trans-4'-butycyclohexyl)ethyl]propane-1,3-diol was prepared in the same manner as in Steps 1 through 8 of Example 4.

A solution of 2.4 g (0.01 mol) of 2-[2'-(trans-4''-butylcyclohexyl)-ethyl]propane-1,3-diol, 2.8 g (0.01 mol) of 3,4-difluorobenzaldehyde (manufactured by Aldrich) and 0.1 g of TsOH in 50 cm³ of dichloromethane was refluxed for 3 hours over a hot water bath with a Dean-Stark trap. The reaction solution was washed with water and the dichloromethane was distilled off. The residue was recrystallized from a solvent mixture of acetone and methanol to yield 3.0 g (0.008 mol) of trans-2-(3',4'-difluorophenyl)-5-[2'-(trans-4''-butylcyclohexyl)-ethyl]-1,3-dioxane. The phase transition points of this compound, measured by DSC, were:

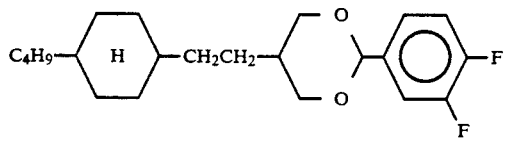

$$C \xrightarrow{83.0°\ C.} N \xrightarrow{87.0°\ C.} I$$

wherein C is the crystal phase, N is the nematic phase, and I is the isotropic liquid phase.

The following are other examples of compounds in accordance with the invention prepared following the procedures of Example 5:

Trans-2-(3',4'-difluorophenyl)-5-[2'-(trans-4''-methylcyclo-hexyl)-ethyl]-1,3-dioxane.

Trans-2-(3',4'-difluorophenyl)-5-[2 trans-4''-ethylcyclohexyl)-ethyl]-1,3-dioxane.

Trans-2-(3',4'-difluorophenyl)-5-[2'-(trans-4''-propylcyclohexyl)-ethyl]-1,3-dioxane.

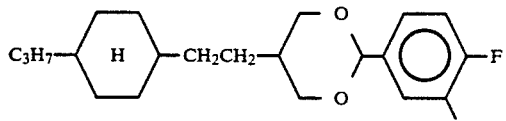

$$C \xrightarrow{80.0°\ C.} N \xrightarrow{88.0°\ C.} I$$

Trans-2-(3',4'-difluorophenyl)-5-[2'-(trans-4''-pentylcyclohexyl)-ethyl]-1,3-dioxane.

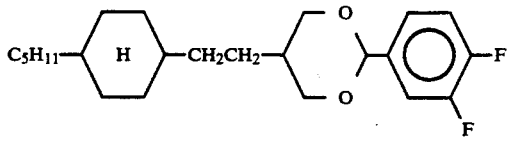

$$C \xrightarrow{86.5°\ C.} N \xrightarrow{93.5°\ C.} I$$

Trans-2-(3',4'-difluorophenyl)-5-[2'-(trans-4''-hexylcyclohexyl)-ethyl]-1,3-dioxane.

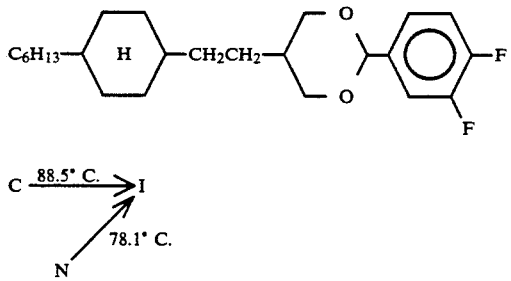

$$C \xrightarrow{88.5°\ C.} I$$
$$\searrow_{78.1°\ C.} N$$

Trans-2-(3',4'-difluorophenyl)-5-[2'-(trans-4''-heptylcyclohexyl)-ethyl]-1,3-dioxane.

Trans-2-(3',4'-difluorophenyl)-5-[2'-(trans-4''-octylcyclohexyl)-ethyl]-1,3-dioxane.

Trans-2-(3',4'-difluorophenyl)-5-[2'-(trans-4''-nonylcyclohexyl)-ethyl]-1,3-dioxane.

EXAMPLE 6

Preparation of trans-2-(4'-cyano-3'-fluorophenyl)-5-[2'-(trans-4''-butylcyclohexyl)ethyl]-1,3-dioxane

Step 1 to Step 3

4-bromo-3-fluorobenzaldehyde was prepared in the same manner as in Steps 4 through 6 of Example 3.

Step 4 to Step 11

2-[2'-(trans-4''-butylcyclohexyl)ethyl]propane-1,3-diol was prepared in the same manner as in Steps 1 through 8 of Example 4.

Step 12

A solution of 6.1 g (0.025 mol) of 2-[2'-(trans-4''-butylcyclohexyl)ethyl]propane-1,3-diol, 5.1 g (0.025 mol) of 4-bromo-3-fluorobenzaldehyde, and g of TsOH in 125 cm³ of dichloromethane was refluxed for 5 hours over a hot water bath with a Dean-Stark trap. The solution was washed with water and the dichloromethane was distilled off. The residue was recrystallized from a solvent mixture of acetone and methanol to yield 8.4 g (0.02 mol) of 2-(4'-bromo-3'-fluorophenyl)-5-[2'-(trans-4''-butylcyclohexyl)ethyl]-1,3-dioxane.

Step 13

8.4 g (0.02 mol) of 2-(4'-bromo-3'-fluorophenyl)-5-[2'-(trans-4''-butylcyclohexyl)ethyl]-1,3-dioxane and 2.7 g (0.03 mol) of CuCN were refluxed in 100 cm³ of NMP for 2 hours. The product was cooled to room temperature and 4 cm³ of EDA was added. The solution was poured into 100 cm³ of ice water, extracted with hexane, and washed with an aqueous solution of EDA and water. The hexane was distilled off. The residue was treated through a silica gel column with chloroform as the solvent and the chloroform was distilled off. The residue was recrystallized from a solvent mixture of acetone and methanol to yield 3.1 g (0.008 mol) of trans-2-(4'-cyano-3'fluorophenyl)-5-[2'-(trans-4''-butylcyclohexyl)ethyl]-1,3-dioxane. The phase transition points of this compound, measured by DSC, were:

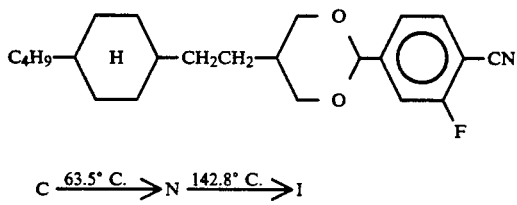

wherein C is the crystal phase, N is the nematic phase, and I is the isotropic liquid phase.

The following are other examples of compounds in accordance with the invention prepared following the procedures of Example 6:

Trans-2-(4'-cyano-3'-fluorophenyl)-5-[2'-(trans-4''-methylcyclohexyl)-ethyl]-1,3-dioxane Trans-2-(4'-cyano-3'-fluorophenyl)-5-[2'-(trans-4''-ethylcyclohexyl)-ethyl]-1,3-dioxane Trans-2-(4'-cyano-3'-fluorophenyl)-5-[2'-(trans-4''-propylcyclohexyl)-ethyl]-1,3-dioxane

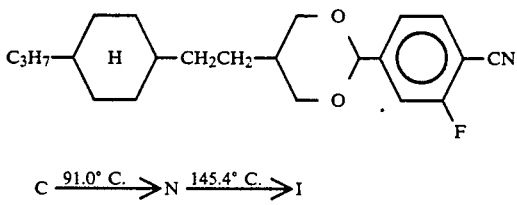

Trans-2-(4'-cyano-3'-fluorophenyl)-5-[2'-(trans-4''-pentylcyclohexyl)-ethyl]-1,3-dioxane

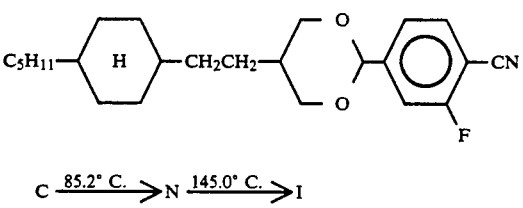

Trans-2-(4'-cyano-3'-fluorophenyl)-5-[2'-(trans-4''-hexylcyclohexyl)-ethyl]-1,3-dioxane

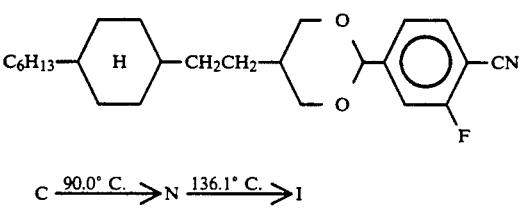

Trans-2-(4'-cyano-3'-fluorophenyl)-5-[2'-(trans-4''-heptylcyclohexyl)-ethyl]-1,3-dioxane Trans-2-(4'-cyano-3'-fluorophenyl)-5-[2,-(trans-4''-octylcyclohexyl)-ethyl]-1,3-dioxane Trans-2-(4'-cyano-3'-fluorophenyl)-5-[2'-(trans-4''-nonylcyclohexyl)-ethyl]-1,3-dioxane Trans-2-(4'-cyano-3'-fluorophenyl)-5-[2'-(trans-4''-decylcyclohexyl)-ethyl]-1,3-dioxane

EXAMPLE 7

Preparation of trans-2-(4'-cyanophenyl)-5-(trans-4'-butylcyclohexyl)-1,3-dioxane Step 1 to Step 3

2-(4'-propylcyclohexyl) propane-1,3-diol was prepared in the same manner as in Steps 1 through 3 of Example 1, substituting trans-4-butylcyclohexanol for trans-4-propylcyclohexanol, as the starting material.

In dichloromethane, 4.6 g (0.02 mol) of 2-(4'-butylcyclohexyl) propane-1,3-diol, 3.2 g (0.024 mol) of 4-cyanobenzaldehyde, and 0.1 g of TsOH were refluxed for three hours over a hot water bath fitted with a Dean-Stark trap and the water formed was continuously removed from the reaction system. The reaction solution was washed with water and the dichloromethane was distilled off. The distillation residue was recrystallized from a solvent mixture of acetone and methanol to yield 1.1 g (0.004 mol) of trans-2-(4'-cyanophenyl)-5-(trans-4'-butylcyclohexyl)-1,3-dioxane. The phase transition points of this compound, measured by DSC, were:

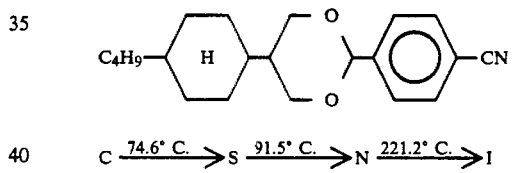

The following are other examples of the compound prepared following the procedures of Example 7.

Trans-2-(4'-cyanophenyl)-5-(trans-4'-ethylcyclohexyl)-1,3-dioxane

Trans-2-(4'-cyanophenyl)-5-(trans-4'-propylcyclohexyl)-1,3-dioxane

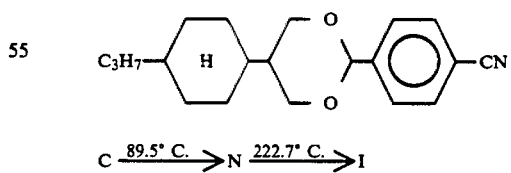

Trans-2-(4'-cyanophenyl)-5-(trans-4'-pentylcyclohexyl)-1,3-dioxane

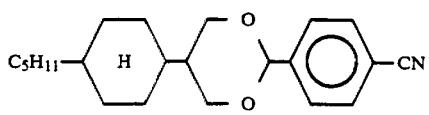

Trans-2-(4'-cyanophenyl)-5-(trans-4'-hexylcyclohexyl-1,3-dioxane

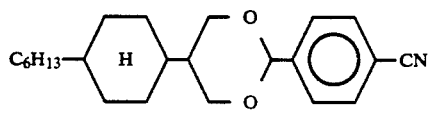

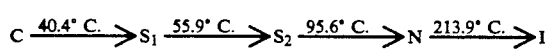

EXAMPLE 8

Preparation of trans-2-(4'-cyanophenyl)-5-[2'-(trans-4'-butylcyclohexyl) ethyl]-1,3-dioxane Step 1 to Step 8

2-[2'-(trans-4'-butylcyclohexyl) ethyl]propane-1,3-diol was prepared in the same manner as in Steps 1 through 8 of Example 4.

Step 9

A solution of 4.9 g (0.02 mol) of 2-[2'-(trans-4'-butylcyclohexyl) ethyl]propane-1,3-diol, 3.2 g (0.024 mol) of 4-cyanobenzaldehyde and 0.2 g of TsOH in 100 cm³ of dichloroethane was refluxed for three hours over a hot water bath with a Dean-Stark trap. The reaction solution was washed with water and the dichloromethane was distilled off. The residue was recrystallized from a solvent mixture of acetone and methanol to yield 4.9 g (0.014 mol) of trans-2-(4'-cyanophenyl)-5-[2'-(trans-4"-butylcyclohexyl) ethyl]-1,3-dioxane. The phase transition points of this compound, measured by DSC, were:

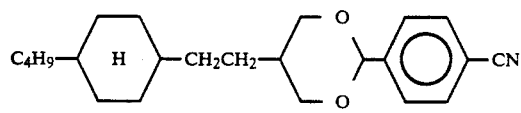

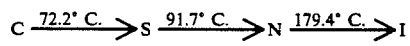

The following are other examples of the compound prepared following the procedures of Example 8.

Trans-2-(4'-cyanophenyl)-5-[2'-(trans-4"-propylcyclohexyl)-ethyl]-1,3-dioxane

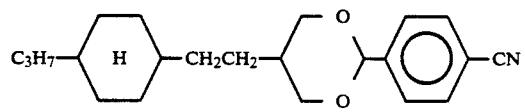

Trans-2-(4'-cyanophenyl)-5-[2'-(trans-4"-pentylcyclohexyl)-ethyl]-1,3-dioxane

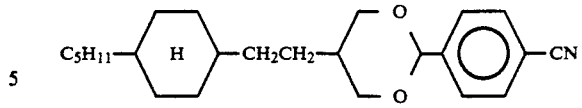

Trans-2-(4'-cyanophenyl)-5-[2'-(trans-4"-hexylcyclohexyl)-ethyl]-1,3-dioxane

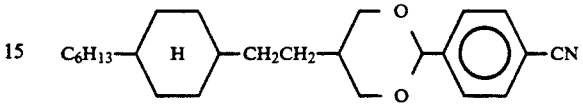

COMPOSITION EXAMPLE 1

Several liquid crystal composition [A1–A6] were prepared by mixing three different compounds of each of compounds II–VII, respectively, in a 1:1:1 ratio wherein Ri sa propyl group, R is a butyl group and R is a pentyl group. Comparative Examples [B1–B2] were prepared in the same manner by mixing three compounds of each of compounds VIII and IX, respectively, in a 1:1:1 ratio wherein R is a propyl group, a butyl group, and a pentyl group.

Liquid crystal composition [A1]:

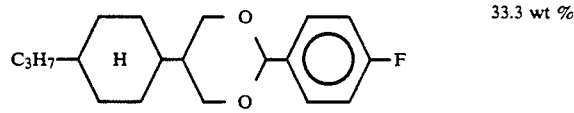

33.3 wt %

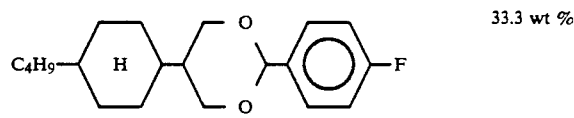

33.3 wt %

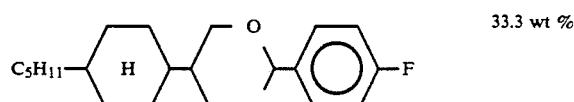

33.3 wt %

Liquid crystal composition [A2]:

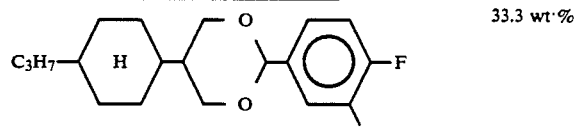

33.3 wt %

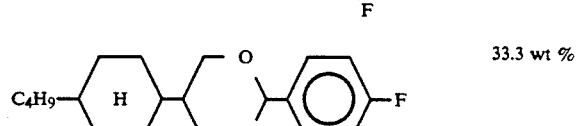

33.3 wt %

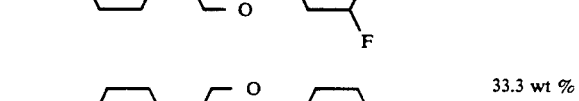

33.3 wt %

Liquid crystal composition [A3]:

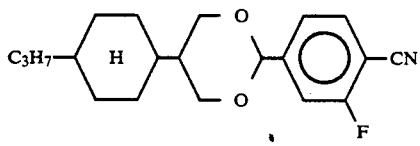 33.3 wt %

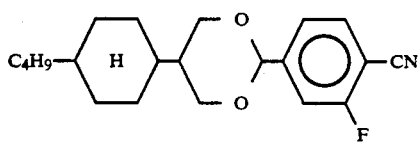 33.3 wt %

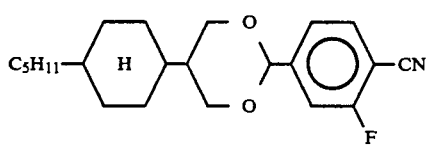 33.3 wt %

Liquid crystal composition [A4]:

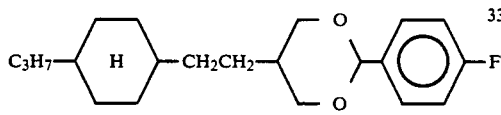 33.3 wt %

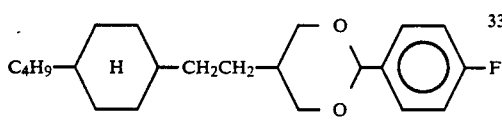 33.3 wt %

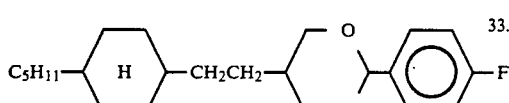 33.3 wt %

Liquid crystal composition [A5]:

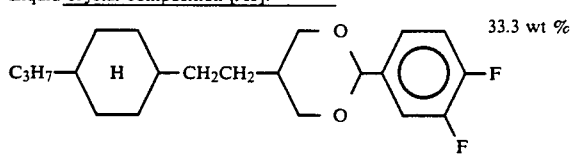 33.3 wt %

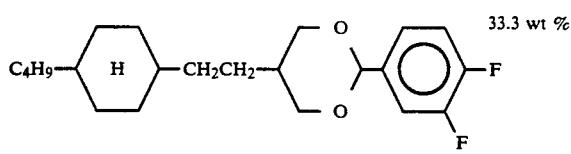 33.3 wt %

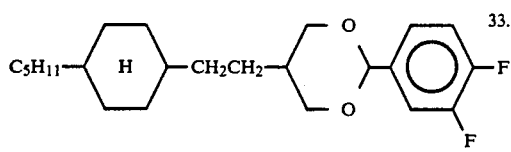 33.3 wt %

Liquid crystal composition [A6]:

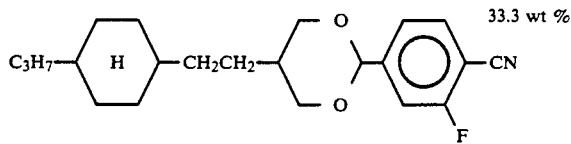 33.3 wt %

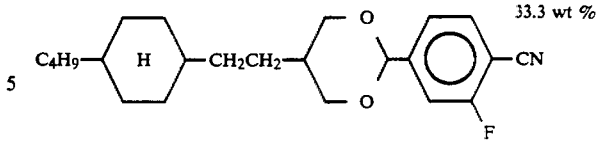 33.3 wt %

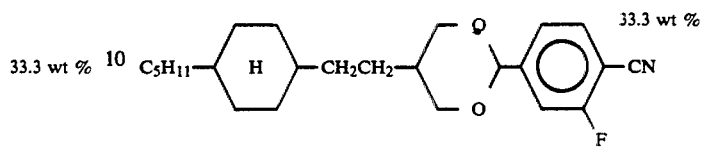 33.3 wt %

Liquid crystal composition [B1]:

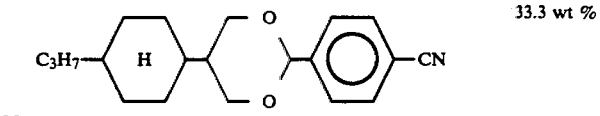 33.3 wt %

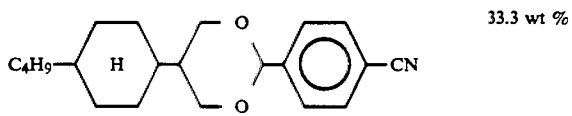 33.3 wt %

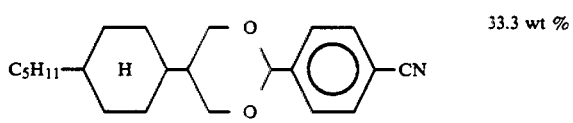 33.3 wt %

Liquid crystal composition [B2]:

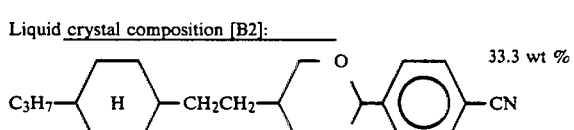 33.3 wt %

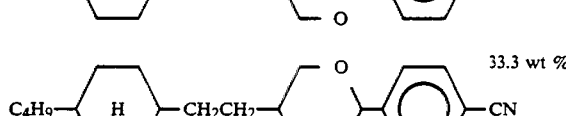 33.3 wt %

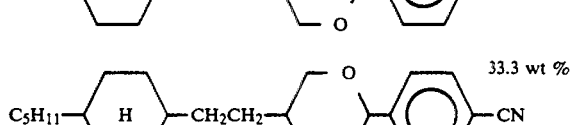 33.3 wt %

Forty liquid crystal compositions were prepared by including 10 wt %, 20 wt %, 30 wt %, 40 wt % and 50 wt % of liquid crystal compositions [A1–A6] and [B1–B2] in 90 wt %, 80 wt %, 70 wt %, 60 wt % and 50 wt %, respectively, of a commercially available liquid crystal composition ZLI-1565 (manufactured by Merck Inc.). Each of the compositions remained at −20° C. for 500 hours and was examined for crystal formation. The results are shown in Table 4.

TABLE 4

| ZLI-1565 | 90 wt % | 80 wt % | 70 wt % | 60 wt % | 50 wt % |
|---|---|---|---|---|---|
| Composition: | 10 wt % | 20 wt % | 30 wt % | 40 wt % | 50 wt % |
| [A1] | O | O | O | X | X |
| [A2] | O | O | O | O | X |
| [A3] | O | O | O | X | X |
| [A4] | O | O | O | X | X |
| [A5] | O | O | O | O | X |
| [A6] | O | O | O | X | X |
| [B1] | O | O | X | X | X |
| [B2] | O | O | X | X | X | wherein x represents the formation of crystals and O represents the absence of the formation of crystals.

Table 4 shows that 1,3-dioxane derivatives of the invention generally have good compatibility and may be included in conventional liquid crystal compositions up to about 30 weight percent. In particular, the 1,3-dioxane derivatives having two fluoro groups (Compounds III and VI) have excellent compatibility. As shown in Table 4, the liquid crystal compositions including conventional compounds VII and IX have poor compatibility.

COMPOSITION EXAMPLE 2

Several liquid crystal compositions [C1-C6] were prepared by including 10 wt % of a fluoro substituted trans-2-phenyl-5-(trans-4'-butylcyclohexyl)-1,3-dioxane derivative (compounds II-VII wherein R is —C$_4$H$_9$) in ZLI-1565. For comparison, liquid crystal compositions [D1-D4] were prepared by including 10 wt % of the following compounds, respectively, in ZLI-1565:

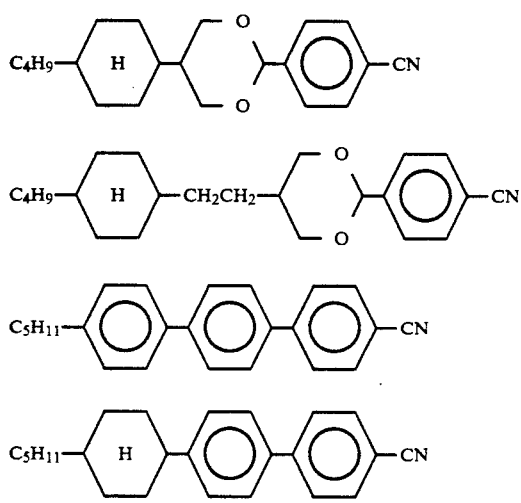

Liquid crystal composition [C1]:
ZLI-1565                90 wt %

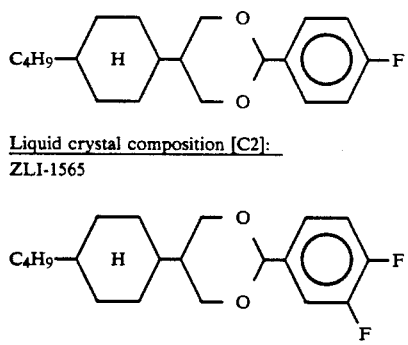

10 wt %

Liquid crystal composition [C2]:
ZLI-1565                90 wt %

10 wt %

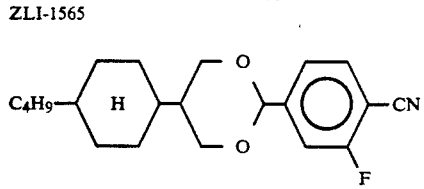

Liquid crystal composition [C3]:
ZLI-1565                90 wt %

10 wt %

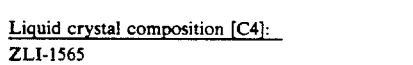

Liquid crystal composition [C4]:
ZLI-1565                90 wt %

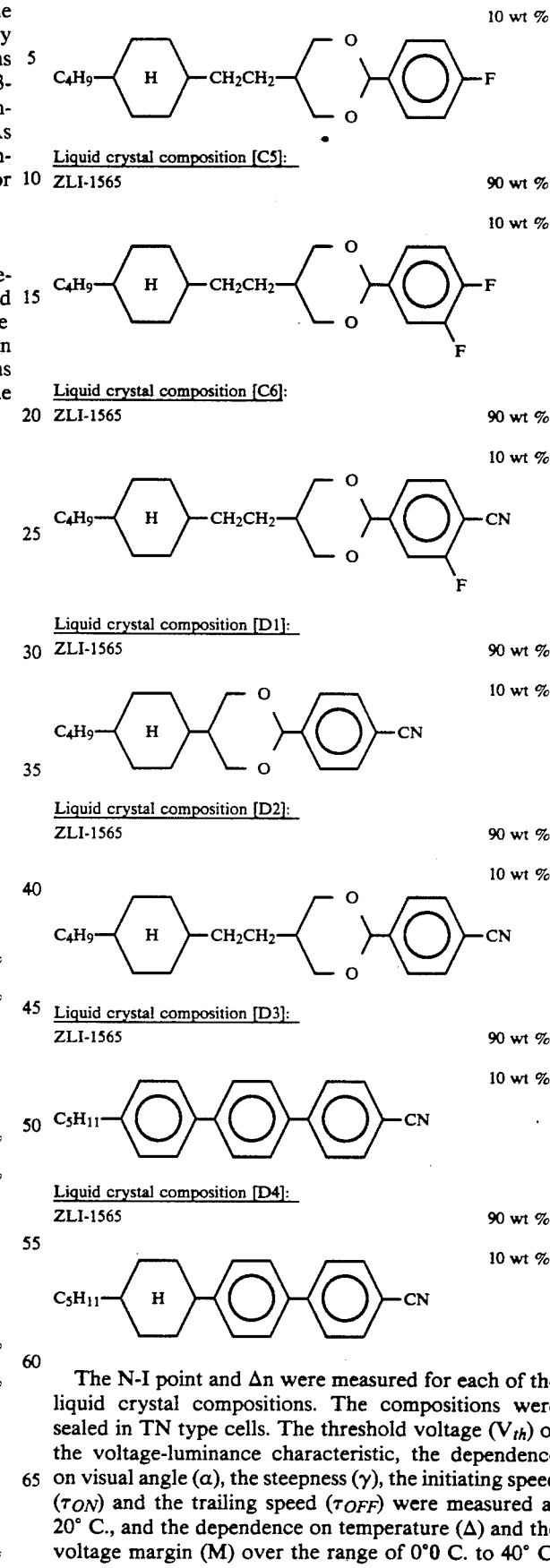

The N-I point and Δn were measured for each of the liquid crystal compositions. The compositions were sealed in TN type cells. The threshold voltage (V$_{th}$) of the voltage-luminance characteristic, the dependence on visual angle (α), the steepness (γ), the initiating speed (τ$_{ON}$) and the trailing speed (τ$_{OFF}$) were measured at 20° C., and the dependence on temperature (Δ) and the voltage margin (M) over the range of 0°0 C. to 40° C.

were determined, where $\alpha$, $\gamma$, $\Delta T$, and M were defined by the following formulae:

$$\alpha = \frac{V_{th}(T = 20°\text{ C. } \phi = 10°)}{V_{th}(T = 20°\text{ C. } \phi = 40°)}$$

$$\gamma = \frac{V_{sat}(T = 20°\text{ C. } \phi = 10°)}{V_{th}(T = 20°\text{ C. } \phi = 10°)}$$

$$\Delta T = V_{th}(T = 0°\text{ C., } \phi = 10°) - V_{th}(T = 40°\text{ C., } \phi = 10°)$$

$$M = \frac{V_{th}(T = 40°\text{ C. }\phi = 40°) - V_{sat}(T = 0°\text{ C., }\phi = 10°)}{V_{th}(T = 40°\text{ C. }\phi = 40°) + V_{sat}(T = 0°\text{ C., }\phi = 10°)} \times 100$$

wherein $V_{th}$ and $V_{sat}$ are the voltage at 10% and 50% of light transmittance, respectively; T is the temperature; $\phi$ is the visual angle (with the front side 0°), and M is a value at ⅓ bias-⅓ duty. The results are shown in Table 5.

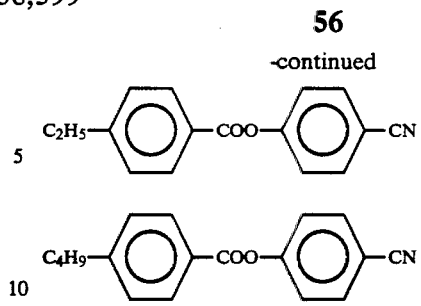

Compositions [E1-E6] were prepared by mixing 10 wt % of Compounds II-VII, wherein R is —C₄H₉, respectively, with composition [M1]. For purpose of comparison, liquid crystal compositions [F1-F4] were prepared by mixing 10 wt % of conventional compounds VIII and IX, wherein R is —C₄H₉, and conventional compounds X and XI wherein R is —C₅H₁₁, respectively, with composition [M1].

TABLE 5

| Composition | N—I Point | Δn | $V_{th}$(V) | α | γ | $\tau_{ON}$(ms) | $\tau_{OFF}$(ms) | ΔT(V) | M(%) |
|---|---|---|---|---|---|---|---|---|---|
| [C1] | 92.1 | 0.124 | 2.51 | 1.30 | 1.45 | 58 | 124 | −0.28 | 9.2 |
| [C2] | 89.5 | 0.123 | 2.42 | 1.29 | 1.48 | 56 | 127 | −0.30 | 8.6 |
| [C3] | 93.8 | 0.130 | 2.19 | 1.29 | 1.38 | 60 | 113 | −0.31 | 9.6 |
| [C4] | 89.0 | 0.124 | 2.50 | 1.31 | 1.49 | 52 | 121 | −0.25 | 8.9 |
| [C5] | 86.5 | 0.123 | 2.38 | 1.30 | 1.47 | 54 | 125 | −0.30 | 9.5 |
| [C6] | 92.7 | 0.127 | 2.23 | 1.29 | 1.41 | 68 | 132 | −0.31 | 9.8 |
| [D1] | 99.3 | 0.130 | 2.38 | 1.30 | 1.48 | 57 | 130 | −0.31 | 8.4 |
| [D2] | 95.2 | 0.128 | 2.45 | 1.31 | 1.48 | 59 | 136 | −0.31 | 8.2 |
| [D3] | 100.8 | 0.149 | 2.52 | 1.30 | 1.49 | 49 | 102 | −0.29 | 8.2 |
| [D4] | 99.4 | 0.139 | 2.48 | 1.32 | 1.46 | 48 | 108 | −0.29 | 8.8 |

COMPOSITION EXAMPLE 3

A liquid crystal composition [M1] including the following Nn type phenylcyclohexane carboxylic esters and Np type cyanophenylbenzoic esters were prepared.

Liquid crystal composition [M1]:

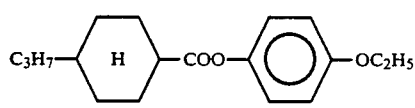  7.9 wt %

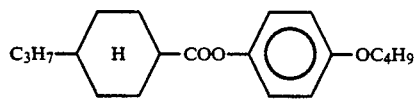  20.5 wt %

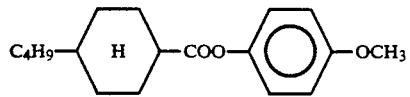  15.9 wt %

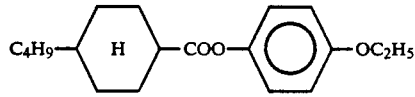  16.0 wt %

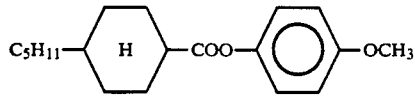  17.5 wt %

-continued

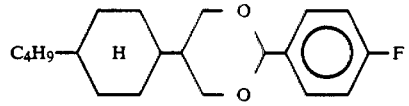  11.1 wt %

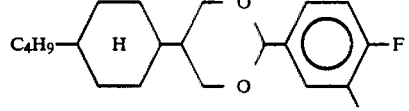  11.1 wt %

Liquid crystal composition [E1]:

[M1]  90 wt %

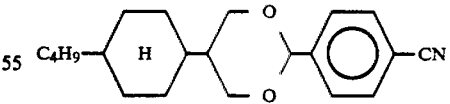  10 wt %

Liquid crystal composition [E2]:

[M1]  90 wt %

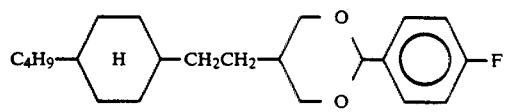  10 wt %

Liquid crystal composition [E3]:

[M1]  90 wt %

C₄H₉—⟨H⟩—⟨O-O⟩—CN  10 wt %

Liquid crystal composition [E4]:

[M1]  90 wt %

C₄H₉—⟨H⟩—CH₂CH₂—⟨O-O⟩—F  10 wt %

Liquid crystal composition [E5]:

[M1]  90 wt %

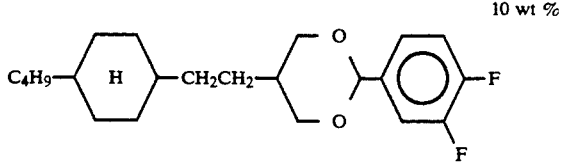 10 wt %

Liquid crystal composition [E6]:
[M1] 90 wt %
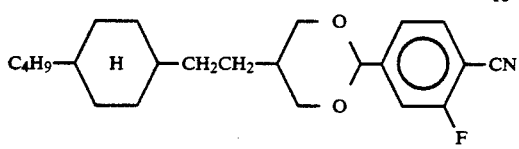 10 wt %

Liquid crystal composition [F1]:
[M1] 90 wt %
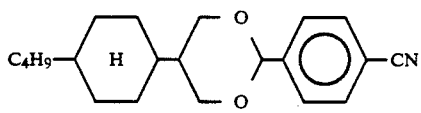 10 wt %

Liquid crystal composition [F2]:
[M1] 90 wt %
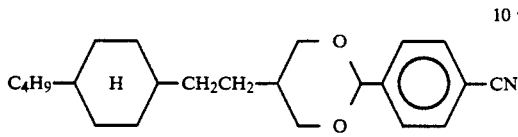 10 wt %

Liquid crystal composition [F3]:
[M1] 90 wt %
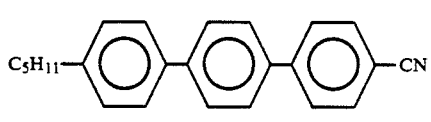 10 wt %

Liquid crystal composition [F4]:
[M1] 90 wt %
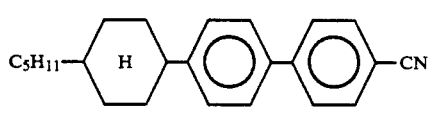 10 wt %

The N-I point, $\Delta n$, $V_{th}$, $\alpha$, $\gamma$, $\tau_{on}$, $\tau_{off}$, $\Delta$ and M were determined in the same manner as in Composition Example 2. The results are shown in Table 6.

COMPOSITION EXAMPLE 4

A liquid crystal composition [M2] including the following phenylcyclohexane carboxylic esters and Np type cyanobiphenyl and Nn type cyanophenyl pyrimidine compounds were prepared.

Liquid crystal composition [M2]:
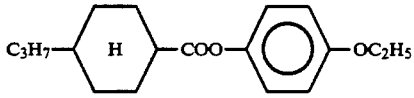 17.8 wt %
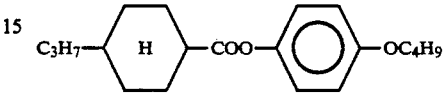 17.8 wt %
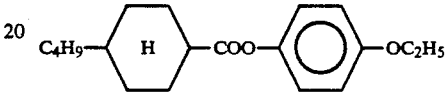 17.8 wt %
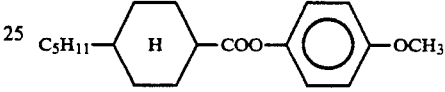 18.8 wt %
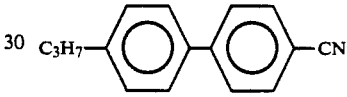 11.1 wt %
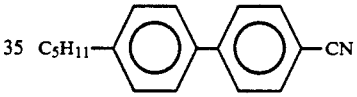 11.1 wt %
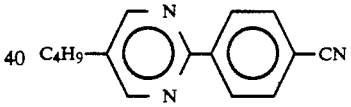 5.6 wt %

Compositions [G1-G6] were prepared by mixing 10 wt % of Compounds II-VII, wherein R is —C$_4$H$_9$, respectively, with composition [M2]. For purpose of comparison, liquid crystal compositions [H1-H4] were prepared by mixing 10 wt % of conventional compounds VIII and IX, wherein R is —C$_4$H$_9$ and conventional compounds X and XI wherein R is —C$_5$H$_{11}$, respectively, with composition [M2].

Liquid crystal composition [G1]:
[M2] 90 wt %

TABLE 6

| Composition | N—I Point | Δn | $V_{th}$(V) | α | γ | $\tau_{ON}$(ms) | $\tau_{OFF}$(ms) | ΔT(V) | M(%) |
|---|---|---|---|---|---|---|---|---|---|
| [E1] | 66.3 | 0.101 | 1.84 | 1.25 | 1.43 | 96 | 200 | −0.30 | 10.6 |
| [E2] | 64.6 | 0.101 | 1.73 | 1.23 | 1.41 | 93 | 204 | −0.34 | 10.5 |
| [E3] | 69.3 | 0.105 | 1.68 | 1.27 | 1.45 | 100 | 211 | −0.32 | 9.3 |
| [E4] | 64.2 | 0.101 | 1.85 | 1.25 | 1.44 | 95 | 211 | −0.31 | 10.7 |
| [E5] | 63.0 | 0.101 | 1.78 | 1.23 | 1.40 | 112 | 218 | −0.34 | 10.3 |
| [E6] | 67.5 | 0.105 | 1.70 | 1.27 | 1.45 | 102 | 231 | −0.33 | 9.4 |
| [F1] | 72.0 | 0.107 | 1.78 | 1.27 | 1.43 | 99 | 210 | −0.32 | 9.5 |
| [F2] | 70.2 | 0.106 | 1.77 | 1.27 | 1.42 | 109 | 228 | −0.32 | 9.9 |
| [F3] | 73.5 | 0.127 | 1.83 | 1.28 | 1.44 | 90 | 196 | −0.26 | 10.1 |
| [F4] | 73.9 | 0.117 | 1.89 | 1.29 | 1.45 | 85 | 189 | −0.25 | 9.8 |

[Structure: C4H9—H—CH(—O—)(—O—)—Ph—F] 10 wt %

Liquid crystal composition [G2]:
[M2] 90 wt %

[Structure: C4H9—H—CH(—O—)(—O—)—Ph(3,4-F2)] 10 wt %

Liquid crystal composition [G3]:
[M2] 90 wt %

[Structure: C4H9—H—CH(—O—)(—O—)—Ph(CN, F)] 10 wt %

Liquid crystal composition [G4]:
[M2] 90 wt %

[Structure: C4H9—H—CH2CH2—CH(—O—)(—O—)—Ph—F] 10 wt %

[M2] 90 wt %

[Structure: C4H9—H—CH2CH2—CH(—O—)(—O—)—Ph(3,4-F2)] 10 wt %

Liquid crystal composition [G6]:
[M2] 90 wt %

[Structure: C4H9—H—CH2CH2—CH(—O—)(—O—)—Ph(CN, F)] 10 wt %

Liquid crystal composition [H1]:
[M2] 90 wt %

[Structure: C4H9—H—CH(—O—)(—O—)—Ph(CN, F)] 10 wt %

Liquid crystal composition [H2]:
[M2] 90 wt %

[Structure: C4H9—H—CH2CH2—CH(—O—)(—O—)—Ph(CN, F)] 10 wt %

Liquid crystal composition [H3]:
[M2] 90 wt %

[Structure: C5H11—Ph—Ph—Ph—CN] 10 wt %

Liquid crystal composition [H4]:
[M2] 90 wt %

[Structure: C5H11—H—Ph—Ph—CN] 10 wt %

The N-I point, $\Delta n$, $V_{th}$, $\alpha$, $\gamma$, $\tau_{on}$, $\tau_{off}$, $\Delta T$ and M were determined in the same manner as in Composition Example 2. The results are shown in Table 7.

TABLE 7

| Composition | N—I Point | $\Delta n$ | $V_{th}$(V) | $\alpha$ | $\gamma$ | $\tau_{ON}$(ms) | $\tau_{OFF}$(ms) | $\Delta T$(V) | M(%) |
|---|---|---|---|---|---|---|---|---|---|
| [G1] | 64.5 | 0.120 | 2.05 | 1.23 | 1.39 | 73 | 144 | −0.53 | 5.6 |
| [G2] | 62.7 | 0.118 | 1.99 | 1.22 | 1.38 | 75 | 148 | −0.55 | 4.5 |
| [G3] | 67.5 | 0.121 | 1.88 | 1.26 | 1.43 | 70 | 150 | −0.46 | 7.0 |
| [G4] | 63.2 | 0.119 | 2.03 | 1.24 | 1.42 | 66 | 140 | −0.41 | 8.3 |
| [G5] | 61.2 | 0.118 | 1.96 | 1.24 | 1.42 | 68 | 141 | −0.54 | 5.4 |
| [G6] | 66.1 | 0.123 | 1.84 | 1.25 | 1.41 | 77 | 150 | −0.42 | 8.0 |
| [H1] | 70.8 | 0.126 | 1.94 | 1.25 | 1.40 | 75 | 152 | −0.40 | 8.1 |
| [H2] | 69.1 | 0.124 | 1.99 | 1.27 | 1.44 | 72 | 154 | −0.38 | 8.3 |
| [H3] | 73.6 | 0.145 | 2.06 | 1.26 | 1.39 | 67 | 134 | −0.46 | 7.4 |
| [H4] | 72.2 | 0.136 | 2.07 | 1.27 | 1.44 | 67 | 143 | −0.36 | 8.5 |

COMPOSITION EXAMPLE 5

A liquid crystal composition [M3] including the following Nn type phenylcyclohexane carboxylic esters, Nn type phenylbenzoic esters, Np type cyanophenylbenzoic esters, and Np type cyanophenylcyclohexane carboxylic esters.

Liquid crystal composition [M3]:

[Structure: C3H7—H—COO—Ph—OC4H9] 17.8 wt %

[Structure: C4H9—H—COO—Ph—OC2H5] 17.8 wt %

[Structure: C5H11—H—COO—Ph—OCH3] 17.8 wt %

-continued
Liquid crystal composition [M3]:

CH₃O—⌬—COO—⌬—C₅H₁₁    11.1 wt %

C₆H₁₃—⌬—⌬—COO—⌬—C₅H₁₁    11.1 wt %

C₂H₅—⌬—COO—⌬—CN    13.3 wt %

C₅H₁₁—(H)—COO—⌬—CN    11.1 wt %

Compositions [I1–I6] were prepared by mixing 10 wt % of Compounds II–VII, wherein R is —C₄H₉, respectively, with composition [M3]. For purpose of comparison, liquid crystal compositions [J1–J4] were prepared by mixing 10 wt % of conventional compounds VII an IX, wherein R is —C₄H₉ and conventional compounds X and XI, wherein R is —C₅H₁₁, respectively, with composition [M3].

Liquid crystal composition [I1]:
[M3]    90 wt %

C₄H₉—(H)—CH₂—O—CH—⌬—F    10 wt %
              \O—/

Liquid crystal composition [I2]:
[M3]    90 wt %

C₄H₉—(H)—CH₂—O—CH—⌬—F    10 wt %
              \O—/    F

Liquid crystal compositon [I3]:
[M3]    90 wt %

C₄H₉—(H)—CH₂—O—CH—⌬—CN    10 wt %
              \O—/    F

Liquid crystal composition [I4]:
[M3]    90 wt %

C₄H₉—(H)—CH₂CH₂—O—CH—⌬—F    10 wt %
                \O—/

Liquid crystal composition [I5]:
[M3]    90 wt %

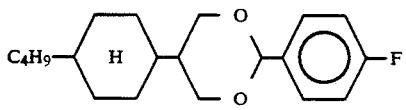    10 wt %

C₄H₉—(H)—CH₂CH₂—O—CH—⌬—F
                \O—/    F

Liquid crystal composition [I6]:
[M3]    90 wt %

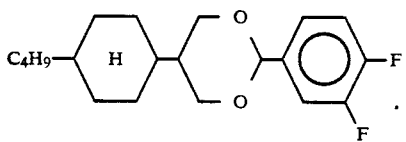    10 wt %

C₄H₉—(H)—CH₂CH₂—O—CH—⌬—CN
                \O—/    F

Liquid crystal composition [J1]:
[M3]    90 wt %

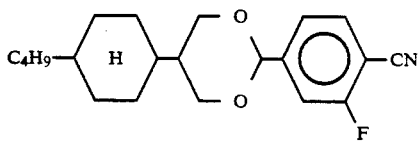    10 wt %

C₄H₉—(H)—CH—O—CH—⌬—CN
           \O—/

Liquid crystal composition [IJ2]:
[M3]    90 wt %

C₄H₉—(H)—CH₂CH₂—O—CH—⌬—CN    10 wt %
                \O—/

Liquid crystal composition [J3]:
[M3]    90 wt %

C₅H₁₁—⌬—⌬—⌬—CN    10 wt %

Liquid crystal composition [J4]:
[M3]    90 wt %

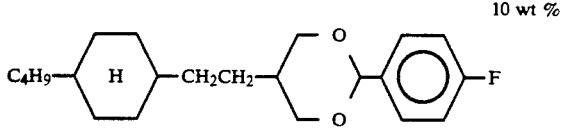    10 wt %

C₅H₁₁—(H)—⌬—⌬—CN

The N-I point, $\Delta n$, $V_{th}$, $\alpha$, $\gamma$, $\tau_{on}$, $\tau_{off}$, $\Delta T$ and M were determined in the same manner as in Composition Example 2. The results are shown in Table 8.

TABLE 8

| Composition | N—I Point | $\Delta n$ | $V_{th}(V)$ | $\alpha$ | $\gamma$ | $\tau_{ON}$(ms) | $\tau_{OFF}$(ms) | $\Delta T(V)$ | M(%) |
|---|---|---|---|---|---|---|---|---|---|
| [I1] | 65.9 | 0.111 | 1.94 | 1.24 | 1.40 | 121 | 247 | −0.34 | 10.3 |
| [I2] | 64.2 | 0.108 | 1.89 | 1.23 | 1.39 | 123 | 240 | −0.38 | 9.4 |
| [I3] | 69.0 | 0.114 | 1.75 | 1.24 | 1.39 | 119 | 234 | −0.35 | 10.0 |
| [I4] | 64.8 | 0.108 | 1.94 | 1.24 | 1.41 | 104 | 210 | −0.33 | 10.7 |
| [I5] | 62.7 | 0.108 | 1.92 | 1.24 | 1.43 | 118 | 248 | −0.37 | 9.4 |
| [I6] | 67.5 | 0.114 | 1.81 | 1.26 | 1.44 | 123 | 256 | −0.36 | 8.4 |
| [J1] | 72.5 | 0.116 | 1.87 | 1.24 | 1.38 | 128 | 240 | −0.34 | 10.0 |
| [J2] | 70.6 | 0.116 | 1.90 | 1.25 | 1.40 | 125 | 253 | −0.33 | 10.0 |
| [J3] | 74.4 | 0.136 | 2.03 | 1.27 | 1.47 | 108. | 228 | −0.33 | 9.2 |

TABLE 8-continued

| Composition | N—I Point | Δn | $V_{th}$(V) | α | γ | $\tau_{ON}$(ms) | $\tau_{OFF}$(ms) | ΔT(V) | M(%) |
|---|---|---|---|---|---|---|---|---|---|
| [J4] | 73.8 | 0.124 | 2.03 | 1.28 | 1.47 | 108 | 238 | −0.32 | 9.7 |

COMPOSITION EXAMPLE 6

A liquid crystal composition [N] was prepared by mixing Nn type phenylcyclohexane carboxylic ester derivatives, Np type cyanophenyldioxane derivatives, an Np type cyanophenylcyclohexane carboxylic ester derivative and trans-1-(4'-cyano-3'-fluorophenyl)-5-(trans-4'-alkylcyclohexyl)-1,3-dioxanes derivatives (compound IV) as shown below:

8.9 wt %

$C_3H_7$—H—COO—⌬—$OC_4H_9$ 7.0 wt %

$C_4H_9$—H—COO—⌬—$OC_2H_5$ 7.5 wt %

$C_5H_{11}$—H—COO—⌬—$OCH_3$ 10.4 wt %

$C_2H_5$—[dioxane]—⌬—CN 15.6 wt %

$C_4H_9$—[dioxane]—⌬—CN 15.6 wt %

$C_5H_{11}$—[dioxane]—⌬—CN 10.0 wt %

$C_3H_7$—H—[dioxane]—⌬—CN, F 10.0 wt %

$C_4H_9$—H—[dioxane]—⌬—CN, F 10.0 wt %

$C_5H_{11}$—H—[dioxane]—⌬—CN, F

-continued 5.0 wt %

$C_5H_{11}$—H—COO—⌬—CN

The N-I point and Δn were measured and the composition was sealed in a 6.3 μm thick TN type cell. $V_{th}$, α, γ, $\tau_{on}$, $\tau_{off}$, ΔT and M were determined in the same manner as in composition Example 2. The results are shown in Table 9.

COMPOSITION EXAMPLE 7

A liquid crystal composition [0] was prepared by mixing Nn type phenylcyclohexane carboxylic ester derivatives, Np type cyanophenyl dioxane derivatives, Np type cyanophenylcyclohexane carboxylic ester derivatives, Nn type phenylcyclohexylcyclohexane carboxylic ester derivatives and trans-2-(4'-cyano-3'-fluorophenyl)-5-(trans-4'-alkylcyclohexyl)-1,3-dioxanederivatives (compound IV) as shown below:

10.3 wt %

$C_3H_7$—H—COO—⌬—$OC_4H_9$ 8.0 wt %

$C_4H_9$—H—COO—⌬—$OC_2H_5$ 8.7 wt %

$C_5H_{11}$—H—COO—⌬—$OCH_3$ 12.0 wt %

$C_2H_5$—[dioxane]—⌬—CN 18.0 wt %

$C_4H_9$—[dioxane]—⌬—CN 18.0 wt %

$C_5H_{11}$—[dioxane]—⌬—CN 5.0 wt %

$C_3H_7$—H—[dioxane]—⌬—CN, F

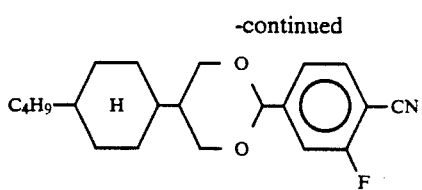 5.0 wt %

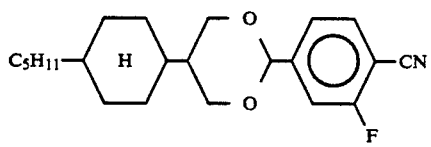 5.0 wt %

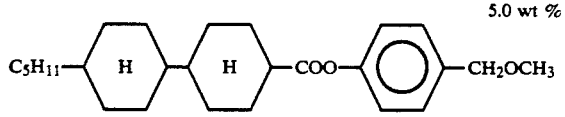 5.0 wt %

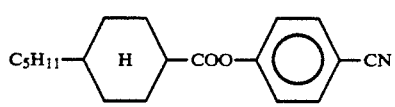 5.0 wt %

The N-I point and Δn were measured and the composition was sealed in a 6.3 μm thick TN type cell. $V_{th}$, α, γ, $τ_{on}$, $τ_{off}$, ΔT and M were determined in the same manner as in Composition Example 2. The results are shown in Table 9.

COMPOSITION EXAMPLE 8

A liquid crystal composition [P] was prepared by mixing Nn type phenylcyclohexane carboxylic ester derivatives, Np type cyanophenyl dioxane derivatives, Np type cyanophenylcyclohexane carboxylic ester derivatives, Np type phenylcyclohexylcyclohexane carboxylic ester derivatives and trans-2-(4'-cyano-3'-fluorophenyl)-5-(trans-4''-alkylcyclohexyl)-1,3-dioxanederivatives (compound VII) as shown below:

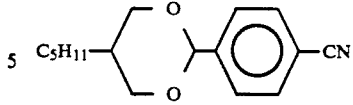 8.9 wt %

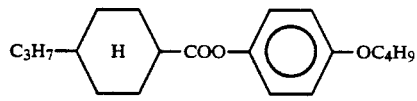 7.0 wt %

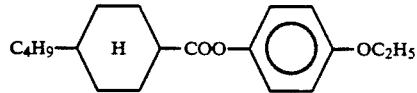 7.5 wt %

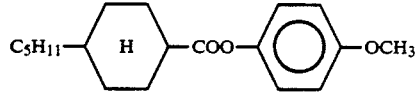 10.4 wt %

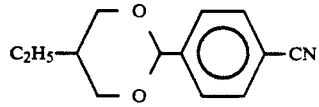 15.6 wt %

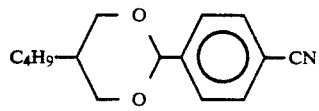

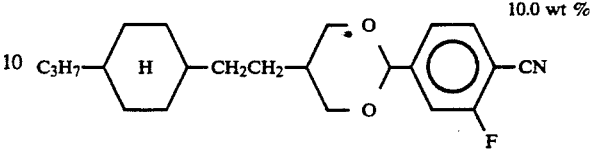 15.6 wt %

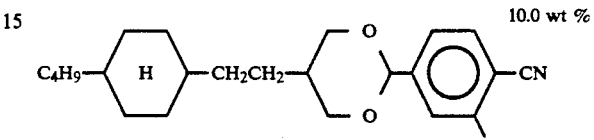 10.0 wt %

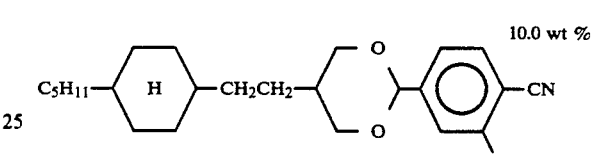 10.0 wt %

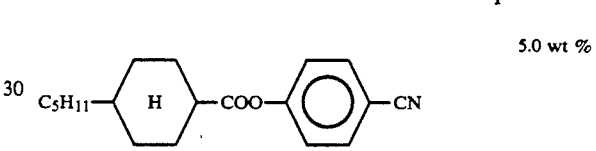 10.0 wt %

5.0 wt %

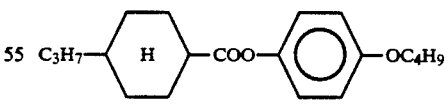

The N-I point and Δn were measured and the composition was sealed in a 6.3 μm thick TN type cell. $V_{th}$, α, γ, $τ_{on}$, $τ_{off}$, ΔT and M were determined in the same manner as in Composition Example 2. The results are shown in Table 9.

COMPOSITION EXAMPLE 9

A liquid crystal composition [Q] was prepared by mixing Nn type phenylcyclohexane carboxylic ester derivatives, Np type cyanophenyl dioxane derivatives, Np type cyanophenylcyclohexane carboxylic ester derivatives, Nn type phenylcyclohexylcyclohexane carboxylic ester derivatives and trans-2-(4'-cyano-3'-fluorophenyl)-5-[2'-(trans-4''-alkylcyclohexyl)ethyl]-1,3-dioxanes derivatives (compound VII) as shown below:

10.3 wt %

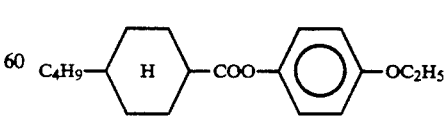 8.0 wt %

8.7 wt %

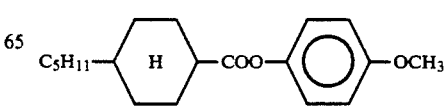

-continued

C₂H₅—[dioxane]—[phenyl]—CN  12.8 wt %

C₄H₉—[dioxane]—[phenyl]—CN  18.0 wt %

C₅H₁₁—[dioxane]—[phenyl]—CN  18.0 wt %

C₃H₇—[H]—CH₂CH₂—[dioxane]—[phenyl(F)]—CN  5.0 wt %

C₄H₉—[H]—CH₂CH₂—[dioxane]—[phenyl(F)]—CN  5.0 wt %

C₅H₁₁—[H]—CH₂CH₂—[dioxane]—[phenyl(F)]—CN  5.0 wt %

C₅H₁₁—[H]—[H]—COO—[phenyl]—CH₂OCH₃  5.0 wt %

C₅H₁₁—[H]—COO—[phenyl]—CN  5.0 wt %

The N-I point and Δn were measured and the composition was sealed in a 6.3 μm thick TN type cell. $V_{th}$, α, γ, $\tau_{on}$, $\tau_{off}$, ΔT and M were determined in the same manner as in Composition Example 2. The results are shown in Table 9.

TABLE 9

| Composition | N—I Point | Δn | $V_{th}$(V) | α | γ | $\tau_{ON}$(ms) | $\tau_{OFF}$(ms) | ΔT(V) | M(%) |
|---|---|---|---|---|---|---|---|---|---|
| [N] | 79.5 | 0.112 | 1.24 | 1.29 | 1.45 | 77.3 | 162 | −0.377 | 7.5 |
| [O] | 67.4 | 0.105 | 1.20 | 1.26 | 1.45 | 66.6 | 135 | −0.46 | 6.8 |
| [P] | 72.5 | 0.107 | 1.21 | 1.28 | 1.45 | 80.6 | 162 | −0.383 | 7.0 |
| [Q] | 64.7 | 0.103 | 1.15 | 1.25 | 1.45 | 71.1 | 139 | −0.467 | 6.8 |

As shown in Table 9, liquid crystal compositions [N], [O], [P] and [Q] including 1,3-dioxane derivatives of the invention have small Δn values, require a low driving voltage and may be used in large scale time sharing driving systems.

The 1,3-dioxane derivatives are included in a liquid crystal composition in at least a minimum effective amount to widen the nematic temperature range, widen the visual angle and decrease the driving and the threshold voltage as desired up to about 50 weight percent based on the total weight of the composition. Preferably, between about 3 and 30 weight percent is added and most prefereably between about 5 and 15 weight percent.

As described above, the 1,3-dioxane derivatives in accordance with the invention have high N-I points between about 80° C. and 180° C., small Δn and large positive Δε. In particular, the 1,3-dioxane derivatives including a fluoro group at the 3 position of the phenyl group and a cyano group at the 4 position of the phenyl group have very large positive Δε. Liquid crystal compositions having low threshold and driving voltages and wide visual angles are obtained when the 1,3-dioxane derivatives of the invention are mixed with conventional liquid crystal compounds. Thus, the 1,3-dioxane derivatives of the invention are extremely useful as constituent components for nematic liqud crystal compositions in twisted nematic and super twisted nematic liquid crystal display devices.

It will thus be seen that the objects set forth above, among those made apparent from the preceding description, are efficiently attained and, since certain changes may be made in carrying out the above method and in the composition set forth above without departing from the spirit and scope of the invention, it is intended that all matter contained in the above description shall be interpreted ass illustrative and not in a limiting sense.

It is also to be understood that the following claims are intended to cover all of the generic and specific feasutres of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A 1,3-dioxane derivative represented by the general formula:

R—[H]—A—[dioxane]—[phenyl(Y)]—X wherein R is a linear alkyl group having from 1 to 10 carbon atoms, A is a single covalent bond or a —CH₂CH₂— group; X is F; Y is H or F; the cyclohexane ring and the 1,3-dioxane ring are the trans isomers and the compounds exhibit the nematic phase.

2. The 1,3-dioxane derivative of claim 1, wherein A is a single covalent bond; X is F; Y is H, represented by the formula:

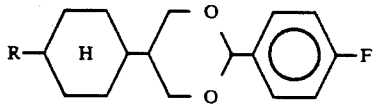

3. The 1,3-dioxane derivative of claim 2, wherein the compound is trans-2-(4'-fluorophenyl)-5-(trans-4'-propylcyclohexyl)-1,3-dioxane represented by the formula:

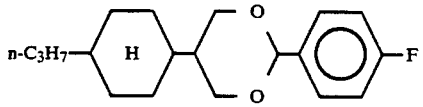

4. The 1,3-dioxane derivative of claim 1, wherein A is a single covalent bond; and X and Y are F represented by the formula:

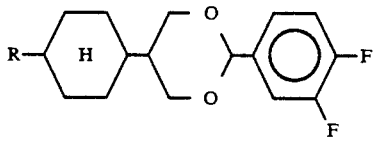

5. The 1,3-dioxane derivative of claim 4, wherein the compound is trans-2-(3',4'-difluorophenyl)-5-(trans-4'-propylcyclohexyl)-1,3-dioxane represented by the formula:

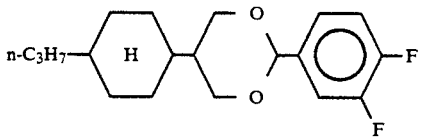

6. The 1,3-dioxane derivative of claim 1, wherein A is —CH₂CH₂—; X is F; and Y is H, represented by the formula:

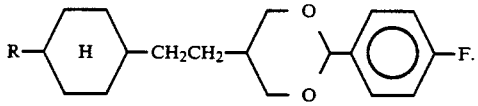

7. The 1,3-dioxane derivative of claim 1, wherein the number of carbon atoms in R is between about 3 and 5.

8. The 1,3-dioxane derivative of claim 1, wherein the number of carbon atoms in R is 4.

9. A 1,3-dioxane derivative, trans-2-(4'-cyano-3'-fluorophenyl)-5-(2'-(trans-4''-butylcyclohexyl)ethyl-1,3-dioxane, represented by the formula:

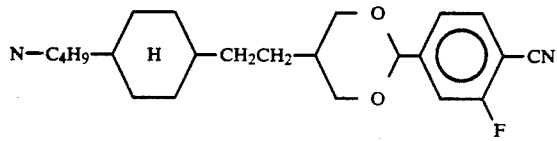

10. A liquid crystal composition comprising an effective amount of at least one 1,3-dioxane derivative for widening the nematic temperature range, decreasing the threshold voltage and widening the visual angle, the dioxane derivative having the general formula:

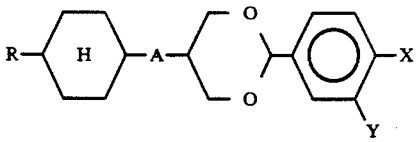

wherein R is a straight chain alkyl group having from 1 to 10 carbon atoms, A is a single covalent bond or a —CH₂CH₂—; X is F; Y is H or F; the cyclohexane ring and the 1,3-dioxane ring are the trans isomers and the compounds exhibit the nematic phase.

11. The liquid crystal composition of claim 10, wherein the dioxane derivative is present between about 1 and 50 weight percent based on the total weight of the composition.

12. The liquid crystal composition of claim 11, wherein the dioxane derivative is present between about 3 and 30 weight percent based on the total weight of the composition.

13. The liquid crystal composition of claim 10, wherein in the 1,3-dioxane derivative, A is a single covalent bond; X is F; and Y is H.

14. The liquid crystal composition of claim 13, wherein the 1,3-dioxane derivative is trans-2-(4'-fluorophenyl)-5-(trans-4'-propylcyclohexyl)-1,3-dioxane.

15. The liquid crystal composition of claim 10, wherein in the 1,3-dioxane derivative, A is a single covalent bond; and X and Y are F.

16. The liquid crystal composition of claim 15, wherein the 1,3-dioxane derivative is trans-2-(3',4'-difluorophenyl)-5-(trans-4'-propylcyclohexyl)-1,3-dioxane.

17. The liquid crystal composition of claim 16, wherein the 1,3-dioxane derivative is trans-2-(4'-cyano-3'-fluorophenyl)-5-(2'-(trans-4''-butylcyclohexyl)ethyl)-1,3-dioxane.

18. A 1,3-dioxane derivative represented by the general formula:

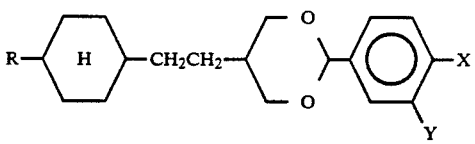

wherein R is a linear alkyl group having from 1 to 10 carbon atoms, X is F or CN; Y is F when X is CN and Y is H or F when X is F; the cyclohexane ring and the 1,3-dioxane ring are the trans isomers and the compounds exhibit the nematic phase.

19. The 1,3-dioxane derivative of claim 18, wherein the compound is trans-2-(4'-fluorophenyl)-5-[2'-(trans-4'-butylcyclohexyl)ethyl]-1,3-dioxane represented by the formula:

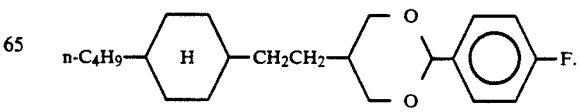

20. The 1,3-dioxane derivative of claim 18, wherein A is —CH₂CH₂—; and X and Y are F, represented by the formula:

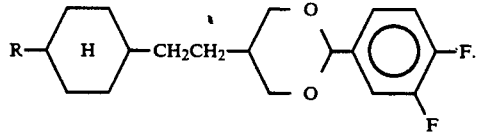

21. The 1,3-dioxane derivative of claim 18, wherein the compound is trans-2-(4'-fluorophenyl)-5-(2'-(trans-4''-butylcyclohexyl)ethyl-1,3-dioxane represented by the formula:

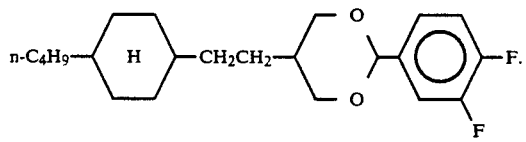

22. The 1,3-dioxane derivative of claim 18, wherein X is CN; and Y is F, represented by the formula:

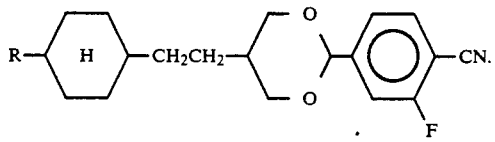

23. The 1,3-dioxane derivative of claim 18, wherein the compound is trans-2-(4'-cyano-3'-fluorophenyl)-5-(2'-trans-4''-butylcyclohexyl)ethyl)-1,3-dioxane represented by the formula:

24. A liquid crystal composition comprising an effective amount of at least one 1,3-dioxane derivative for widening the nematic temperature range, decreasing the threshold voltage and widening the visual angle, the dioxane derivative having the general formula:

wherein R is a straight chain alkyl group having from 1 to 10 carbon atoms; X is F or CN; Y is F when X is CN and Y is H or F when X is F; the cyclohexane ring and the 1,3-dioxane ring are the trans isomers and the compounds exhibit the nematic phase.

25. The liquid crystal composition of claim 24, wherein the 1,3-dioxane derivative is trans-2-(4'-fluorophenyl)-5-[(2'-trans-4'-butylcyclohexyl)ethyl]-1,3-dioxane.

26. The liquid crystal composition of claim 24, wherein in the 1,3-dioxane derivative, X and Y are F.

27. The liquid crystal composition of claim 24, wherein the 1,3-dioxane derivative is trans-2-(3',4'-difluorophenyl)-5-[2'-(trans-4''-butylcyclohexyl)ethyl-1,3-dioxane.

28. The liquid crystal composition of claim 24, wherein in the 1,3-dioxane derivative, X is CN; and Y is F.

29. The liquid crystal composition of claim 24, wherein the 1,3-dioxane derivative is trans-2-(4'-cyano-3'-fluorophenyl)-4-(2'-(trans-4''-butylcyclohexyl)ethyl)-1,3-dioxane.

30. The liquid crystal composition of claim 24, wherein in the 1,3-dioxane derivative, X is F; and Y is H.

* * * * *